United States Patent [19]
Venta et al.

[11] Patent Number: 6,040,143
[45] Date of Patent: Mar. 21, 2000

[54] DNA ENCODING VON WILLEBRAND FACTOR AND METHODS OF USE

[75] Inventors: Patrick J. Venta, Pinckney; George J. Brewer; Vilma Yuzbasiyan-Gurkan, both of Ann Arbor; William D. Schall, Williamston, all of Mich.

[73] Assignee: The Regents of the University of Michigan, Ann Arbor, Mich.

[21] Appl. No.: 08/896,449

[22] Filed: Jul. 18, 1997

Related U.S. Application Data

[60] Provisional application No. 60/020,998, Jul. 19, 1996.

[51] Int. Cl.$^7$ .............................. C07H 21/04; C12Q 1/68; C12P 19/34
[52] U.S. Cl. ................................ 435/6; 435/6; 435/91.1; 435/91.2; 435/325; 536/22.1; 536/23.5; 536/24.31; 536/24.33
[58] Field of Search .................................. 536/22.1, 23.5, 536/24.31, 24.33; 435/325, 252.3, 6, 91.1, 91.2

[56] References Cited

PUBLICATIONS

Avgeris, S. et al., "Plasma von Willebrand Factor Concentration and Thyroid Function in Dogs," *JAVMA* 196:921–92 (1990).
Bakhshi, M.R. et al., "Sequencing of the Primary Adhesion Domain of Bovine von Willebrand Factor," *Biochem. Biophys. Acta* 1132:325–328 (1992).
Benson, R.E. et al., "Efficiency and Precision of Electroimmunoassay for Canine Factor VIII–Related Antigen," *Am. J. Vet. Res.* 44:399–403 (1983).
Bergenhem, N.C.H. et al., "Mutation Creates an Open Reading Frame within the 5′ Untranslated Region of Macaque Erythrocyte Carbonic Anhydrase (CA) I mRNA that Suppresses CA I Expression and Supports the Scanning Model for Translation," *PNAS (USA)* 89:8789–8802 (1992).
Bloom, A.L., "Von Willebrand Factor: Clinical Features of Inherited and Acquired Disorders," *Mayo Clin. Proc.* 66:743–751 (1991).
Bonthron, D. et al., "Nucleotide Sequence of Pre–Pro–von Willebrand Factor cDNA," *Nucleic Acids Res.* 14:7125–7127 (1986).
Brinkhous, K.M. et al., "Pathophysiology of Platelet–Aggegating von Willebrand Factor: Applications of the Venom Coagglutinin vWF Assay," *Ann. New York Acad. Sci.* 370:191–204 (1981).
Brooks, M., "Clinical Features of Canine von Willebrand's Disease," *Proc. 9th ACVIM Forum* pp. 89–91 (1991).
Brooks, M., "Management of Canine von Willebrand's Disease," *Probl. In Vet. Med.* 4:636–646 (1992).
Brooks, M., et al., "Epidemiologic Features of von Willebrand's Disease in Doberman Pinschers, Scottish Terriers, and Shetland Sheepdogs: 260 Cases (1984–1988)," *JAVMA* 200:1123–1127 (1992).
Dodds, W.J., "Von Willebrand's Disease in Dogs," *Mod. Vet. Pract.* 681–686 (1984).
Ginsburg, D. et al., "Molecular Genetics of von Willebrand Disease," *Blood* 79:2507–2519 (1992).
Janel, N. et al., "Comparison of the 5′–Flanking Sequences of the Human and Bovine von Willebrand Factor–Encoding Genes Reveals Alternation of Highly Homologous Domains with Species–Specific Alu–Type Repeats," *Gene* 167:291–295 (1995).
Johnson, G.S. et al., "A Bleeding Disease (von Willebrand's Disease) in a Chesapeake Bay Retriever," *JAVMA* 176:1261–1263 (1980).
Kraus, K.H. et al., "Effect of Desmopressin Acetate on Bleeding Times and Plasma von Willebrand Factor in Doberman Pinscher Dogs with von Willebrand's Disease," *Vet. Surg.* 18:103–109 (1989).
Lankhof, H. et al., "Role of the Glycoprotein Ib–Binding A1 Repeat and the RGD Sequence in Platelet Adhesion to Human Recombinant von Willebrand Factor," *Blood* 86:1035–1042 (1995).
Lavergne, J.M. et al., "Primary Structure of the Factor VIII Binding Domain of Human, Porcine and Rabbit von Willebrand Factor," *Biochem. Biophys. Res. Commun.* 194:1019–1024 (1993).
Mancuso, D.J. et al., "Human von Willebrand Factor Gene and Pseudogene: Structural Analysis and Differentiation by Polymerase Chain Reaction," *Biochemistry* 30:253–269 (1991).
Mancuso, D.J. et al., 1576 An Homologous Canine von Willebrand and Factor Binding Domain for Glycoprotein Ib,: *Thromb Haemost* 69:980 (1993).
Maniatis, T., et al., *Molecular Cloning: A Laboratory Manual*, Cold Spring Harbor Laboratory Press, Cold Spring NY, (1982), at pp. 387–389.
Mansell, P.D. et al., "Changes in Factor VIII Activity and von Willebrand Factor Antigen Concentration with Age in Dogs," *Br. Vet. J.* 148:329–337 (1992).
Meyer, D. et al., "von Willebrand Factor: Structure and Function," *Throm. Haemostasis* 70:99–104 (1993).
O'Brien, P.J. et al., "Use of a DNA–Based Test for the Mutation Associated with Porcine Stress Syndrome (Malignant Hyperthermia) in 10,000 Breeding Swine," *JAVMA* 203:842–851 (1993).
Panciera, D.L. et al., "Plasma von Willebrand Factor Antigen Concentration in Dogs with Hypothyroidism," *JAVMA* 205:1550–1553 (1994).
Porter, C.A. et al., "Evidence of Mammalian Phylogeny from Sequences of Exon 28 of the von Willebrand Factor Gene," *Mol Phylogenet Evol* 5:89–101 (1996).

(List continued on next page.)

*Primary Examiner*—Kenneth R. Horlick
*Assistant Examiner*—Joyce Tung
*Attorney, Agent, or Firm*—Harness, Dickey & Pierce, P.L.C.

[57] ABSTRACT

The complete sequence of the canine von Willebrand Factor cDNA and deduced amino acid sequence is provided. The mutation which causes von Willebrand's Disease in Scottish Terriers, a single base deletion in exon 4, has also been determined. Methods for detecting carriers of the defective vWF gene are also provided.

31 Claims, 9 Drawing Sheets

PUBLICATIONS

Read, M.S. et al., "Venom Coagglutinin for Detection of von Willebrand Factor Activity in Animal Plasmas," *J. Lab. Clin. Med.* 101:74–82 (1983).

Richards, B. et al., "Multiplex PCR Amplification from the CFTR Gene Using DNA Prepared from Buccal Brushes/Swabs," *Human Molecular Genetics* 2:159–163 (1992).

Rosborough, T.K. et al., "Measurement of Canine von Willebrand Factor Using Ristocetin and Polybrene," *J. Lab. Clin. Med.* 96:47–56 (1980).

Rudolph, J.A. et al., "Periodic Paralysis in Quarter Horses: a Sodium Channel Mutation Disseminated by Selective Breeding," *Nat. Genet.* 2:144–147 (1992).

Ruggeri, Z.M., et al., "von Willebrand Factor," *FASEB J.* 7:308–316 (1993).

Sadler, J.E. et al., "Commentary: A New Classification for von Willebrand Disease," *Blood* 84:676–679 (1994).

Sambrook J. et al., "Identification of cDNA Clones of Interest," *Molecular Cloning: A Laboratory Manual*, Second Edition, vol. 2, Cold Spring Harbor Laboratory Press, Cold Spring, NY at pp. 8.46–8.47 (1989).

Shibuya, H. et al., "A Polymorphic (AGGATT)$_n$ Tandem Repeat in an Intron of the Canine von Willebrand Factor Gene," *Anim. Genet* 25:122 (1994).

Shuster, D.E. et al., "Identification and Prevalence of a Genetic Defect that Causes Leukocyte Adhesion Deficiency in Holstein Cattle," *PNAS (USA)* 89:9225–9229 (1992).

Slappendel, R.J., "von Willebrand's Disease in Dutch Kooiker Dogs," *Vet–Q* 17:S21–S22 (1995).

Stirling, Y. et al., "Heamostasis in Normal Pregnancy," *Thromb Haemostasis* 52:176–182 (1984).

Stokol, T. et al., "Stability of von Willebrand Factor and Factor VIII in Canine Cryoprecipitate Under Various Conditions of Storage," *Res. Vet. Sci.* 59:152–155 (1995).

Strauss, H.S. et al., "Elevation of Factor VIII (Antihemophilic Factor) During pregnancy in Normal Persons and in a Patient with von Willebrand's Disease," *New Eng. J. Med.* 269:1251–1252 (1963).

Turrentine, M.A., et al., "Plasma from Donor Dogs, Pretreated with DDAVP, Transfused into a German Shorthair Pointer with Type II von Willebrand's Disease," *Vet. Clin. North Am. Small Anim. Pract.* 18:275 (1988).

Venta, P.J. et al., "Gene–Specific Universal Mammalian Sequence–Tagged Sites: Application to the Canine Genome" *Biochem. Genet.* 34:321–341 (1996).

Verweij, C,L. et al., Expression of Variant von Willebrand Factor (vWF) cDNA in heterologous Cells: Requirement of the Pro–polypeptide in vWF Multimer Formation,: *EMBO J.* 6:2885–2890 (1987).

Wise, R.J. et al., "The Propeptide of von Willebrand Factor Independently Mediates the Assembly of von Willebrand Multimers," *Cell* 52:229–236 (1988).

FIGURE 1A

```
   1 CATTAANAGG TCCTGGCTGG GAGCTTTTTT TTGGGACCAG CACTCCATGT TCAAGGGCAA
  61 ACAGGGGCCA ATTAGGATCA ATCTTTTTC TTTCTTTTTT TAAAAAAAAA AATTCTTCCC
 121 ACTTTGCACA CGGACAGTAG TACATACCAG TAGCTCTCTG CGAGGACGGT GATCACTAAT
 181 CATTTCTCCT GCTTCGTGGC AGATGAGTCC TACCAGACTT GTGAGGGTGC TGCTGGCTCT
 241 GGCCCTCATC TTGCCAGGGA AACTTTGTAC AAAAGGGACT GTTGGAAGGT CATCGATGGC
 301 CCGATGTAGC CTTCTCGGAG GTGACTTCAT CAACACCTTT GATGAGAGCA TGTACAGCTT
 361 TGCGGGAGAT TGCAGTTACC TCCTGGCTGG GGACTGCCAG GAACACTCCA TCTCACTTAT
 421 CGGGGGTTTC CAAAATGACA AAGAGTGAG CCTCTCCGTG TATCTCGGAG AATTTTTCGA
 481 CATTCATTTG TTTGTCAATG GTACCATGCT GCAGGGGACC CAAAGCATCT CCATGCCCTA
 541 CGCCTCCAAT GGGCTGTATC TAGAGGCCGA GGCTGGCTAC TACAAGCTGT CCAGTGAGGC
 601 CTACGGCTTT GTGGCCAGAA TTGATGGCAA TGGCAACTTT CAAGTCCTGC TGTCAGACAG
 661 ATACTTCAAC AAGACCTGTG GGCTGTGTGG CAACTTTAAT ATCTTTGCTG AGGATGACTT
 721 CAAGACTCAA GAAGGGACGT TGACTTCGGA CCCCTATGAC TTTGCCAACT CCTGGGCCCT
 781 GAGCAGTGGG AACAACGGT GCAAACGGGT GTCCCCTCCC AGCAGCCCAT GCAATGTCTC
 841 CTCTGATGAA GTGCAGCAGG TCCTGTGGGA GCAGTGCCAG CTCCTGAAGA GTGCCTCGGT
 901 GTTTGCCCGC TGCCACCCGC TGGTGGACCC TGAGCCTTTT GTCGCCCTGT GTGAAAGGAC
 961 TCTGTGCACC TGTGTCCAGG GGATGGAGTG CCCTTGTGCG GTCCTCCTGG AGTACGCCCG
1021 GGCCTGTGCC CAGCAGGGGA TTGTCTTGTA CGGCTGGACC GACCACAGCG TCTGCCGACC
1081 AGCATGCCCT GCTGGCATGG AGTACAAGGA GTGCGTGTCC CCTTGCACCA GAACTTGCCA
1141 GAGCCTTCAT GTCAAAGAAG TGTGTCAGGA GCAATGTGTA GATGGCTGCA GCTGCCCCGA
1201 GGGCCAGCTC CTGGATGAAG GCCACTGCGT GGGAAGTGCT GAGTGTTCCT GTGTGCATGC
1261 TGGGCAACGG TACCCTCCGG GCGCCTCCCT CTTACAGGAC TGCCACACCT GCATTTGCCG
1321 AAATAGCCTG TGGATCTGCA GCAATGAAGA ATGCCCAGGC GAGTGTCTGG TCACAGGACA
1381 GTCCCACTTC AAGAGCTTCG ACAACAGGTA CTTCACCTTC AGTGGGGTCT GCCACTACCT
1441 GCTGGCCCAG GACTGCCAGG ACCACACATT CTCTGTTGTC ATAGAGACTG TCCAGTGTGC
1501 CGATGACCTG GATGCTGTCT GCACCCGCTC GGTCACCGTC CGCCTGCCTG GACATCACAA
1561 CAGCCTTGTG AAGCTGAAGA ATGGGGGAGG AGTCTCCATG GATGGCCAGG ATATCCAGAT
1621 TCCTCTCCTG CAAGGTGACC TCCGCATCCA GCACACCGTG ATGGCCTCCG TGCGCCTCAG
1681 CTACGGGGAG GACCTGCAGA TGGATTCGGA CGTCCGGGGC AGGCTACTGG TGACGCTGTA
1741 CCCCGCCTAC GCGGGGAAGA CGTGCGGCCG TGGCGGGAAC TACAACGGCA ACCGGGGGGA
1801 CGACTTCGTG ACGCCCGCAG GCCTGGCGGA GCCCCTGGTG GAGGACTTCG GAACGCCTG
1861 GAAGCTGCTC GGGGCCTGCG AGAACCTGCA GAAGCAGCAC CGCGATCCCT GCAGCCTCAA
1921 CCCGCGCCAG GCCAGGTTTG CGGAGGAGGC GTGCGCGCTG CTGACGTCCT CGAAGTTCGA
1981 GCCCTGCCAC CGAGCGGTGG GTCCTCAGCC CTACGTGCAG AACTGCCTCT ACGACGTCTG
2041 CTCCTGCTCC GACGGCAGAG ACTGTCTTTG CAGCGCCGTG GCCAACTACG CCGCAGCCGT
2101 GGCCCGGAGG GGCGTGCACA TCGCGTGGCG GGAGCCGGGC TTCTGTGCGC TGAGCTGCCC
2161 CCAGGGCCAG GTGTACCTGC AGTGTGGGAC CCCCTGCAAC ATGACCTGTC TCTCCCTCTC
2221 TTACCCGGAG GAGGACTGCA ATGAGGTCTG CTTGGAAAGC TGCTTCTCCC CCCCAGGGCT
2281 GTACCTGGAT GAGAGGGAG ATTGTGTGCC CAAGGCTCAG TGTCCCTGTT ACTATGATGG
2341 TGAGATCTTT CAGCCCGAAG ACATCTTCTC AGACCATCAC ACCATGTGCT ACTGTGAGGA
2401 TGGCTTCATG CACTGTACCA CAAGTGGAGG CCTGGGAAGC TGCTGCCCA ACCCGGTGCT
2461 CAGCAGCCCC CGGTGTCACC GCAGCAAAAG GAGCCTGTCC TGTCGGCCCC CCATGGTCAA
2521 GTTGGTGTGT CCCGCTGATA ACCCGAGGGC TGAAGGACTG GAGTGTGCCA AAACCTGCCA
2581 GAACTATGAC CTGCAGTGCA TGAGCACAGG CTGTGTCTCC GGCTGCCTCT GCCCGCAGGG
2641 CATGGTCCGG CATGAAAACA GGTGTGTGGC GCTGGAAAGA TGTCCCTGCT TCCACCAAGG
2701 CCAAGAGTAC GCCCCAGGAG AAACCGTGAA AATTGACTGC AACACTTGTG TCTGTCGGGA
2761 CCGGAAGTGG ACCTGCACAG ACCATGTGTG TGATGCCACT TGCTCTGCCA TCGGCATGGC
2821 GCACTACCTC ACCTTCGACG GACTCAAGTA CCTGTTCCCT GGGGAGTGCC AGTATGTTCT
2881 GGTGCAGGAT TACTGCGGCA GTAACCCTGG GACCTTACGG ATCCTGGTGG GAACGAGGG
2941 GTGCAGCTAC CCCTCAGTGA ATGCAAGAA GCGGGTCACC ATCCTGGTGG AAGGAGGAGA
3001 GATTGAACTG TTTGATGGGG AGGTGAATGT GAAGAAACCC ATGAAGGATG AGACTCACTT
3061 TGAGGTGGTA GAGTCTGGTC AGTACGTCAT TCTGCTGCTG GGCAAGGCAC TCTCTGTGGT
3121 CTGGGACCAC CGCCTGAGCA TCTCTGTGAC CCTGAAGCGG ACATACCAGG AGCAGGTGTG
```

FIGURE 1B

```
3181 TGGCCTGTGT GGGAATTTTG ATGGCATCCA GAACAATGAT TTCACCAGCA GCAGCCTCCA
3241 AATAGAAGAA GACCCTGTGG ACTTTGGGAA TTCCTGGAAA GTGAACCCGC AGTGTGCCGA
3301 CACCAAGAAA GTACCACTGG ACTCATCCCC TGCCGTCTGC CACAACAACA TCATGAAGCA
3361 GACGATGGTG GATTCCTCCT GCAGGATCCT CACCAGTGAT ATTTTCCAGG ACTGCAACAG
3421 GCTGGTGGAC CCTGAGCCAT TCCTGGACAT TTGCATCTAC GACACTTGCT CCTGTGAGTC
3481 CATTGGGGAC TGCACCTGCT TCTGTGACAC CATTGCTGCT TACGCCCACG TCTGTGCCCA
3541 GCATGGCAAG GTGGTAGCCT GGAGGACAGC CACATTCTGT CCCCAGAATT GCGAGGAGCG
3601 GAATCTCCAC GAGAATGGGT ATGAGTGTGA GTGGCGCTAT AACAGCTGTG CCCCTGCCTG
3661 TCCCATCACG TGCCAGCACC CCGAGCCACT GGCATGCCCT GTACAGTGTG TTGAAGGTTG
3721 CCATGCGCAC TGCCCTCCAG GAAAATCCT GGATGAGCTT TTGCAGACCT GCATCGACCC
3781 TGAAGACTGT CCTGTGTGTG AGGTGGCTGG TCGTCGCTTG GCCCCAGGAA AGAAAAATCAT
3841 CTTGAACCCC AGTGACCCTG AGCACTGCCA AATTTGTAAT TGTGATGGTG TCAACTTCAC
3901 CTGTAAGGCC TGCAGAGAAC CCGGAAGTGT TGTGGTGCCC CCACAGATG GCCCCATTGG
3961 CTCTACCACC TCGTATGTGG AGGACACGTC GGAGCCGCCC CTCCATGACT TCCACTGCAG
4021 CAGGCTTCTG GACCTGGTTT TCCTGCTGGA TGGCTCCTCC AAGCTGTCTG AGGACGAGTT
4081 TGAAGTGCTG AAGGTCTTTG TGGTGGGTAT GATGGAGCAT CTGCACATCT CCCAGAAGCG
4141 GATCCGCGTG GCTGTGGTGG AGTACCACGA CGGCTCCCAC GCCTACATCG AGCTCAAGGA
4201 CCGGAAGCGA CCCTCAGAGC TGCGGCGCAT CACCAGCCAG GTGAAGTACG CGGGCAGCGA
4261 GGTGGCCTCC ACCAGTGAGG TCTTAAAGTA CACGCTGTTC CAGATCTTTG GCAAGATCGA
4321 CCGCCCGGAA GCGTCTCGCA TTGCCCTGCT CCTGATGGCC AGCCAGGAGC CCTCAAGGCT
4381 GGCCCGGAAT TTGGTCCGCT ATGTGCAGGG CCTGAAGAAG AAGAAAGTCA TTGTCATCCC
4441 TGTGGGCATC GGGCCCCACG CCAGCCTTAA GCAGATCCAC CTCATAGAGA AGCAGGCCCC
4501 TGAGAACAAG GCCTTTGTGT TCAGTGGTGT GGATGAGTTG GAGCAGCGAA GGGATGAGAT
4561 TATCAACTAC CTCTGTGACC TTGCCCCCGA AGCACCTGCC CCTACTCAGC ACCCCCCAAT
4621 GGCCCAGGTC ACGGTGGGTT CGGAGCTGTT GGGGGTTTCA TCTCCAGGAC CAAAAGGAA
4681 CTCCATGGTC CTGGATGTGG TGTTTGTCCT GGAAGGGTCA GACAAATTG GTGAGGCCAA
4741 CTTTAACAAA AGCAGGGAGT TCATGGAGGA GGTGATTCAG CGGATGGACG TGGGCCAGGA
4801 CAGGATCCAC GTCACAGTGC TGCAGTACTC GTACATGGTG ACCGTGGAGT ACACCTTCAG
4861 CGAGGCGCAG TCCAAGGGCG AGGTCCTACA GCAGGTGCGG GATATCCGAT ACCGGGGTGG
4921 CAACAGGACC AACACTGGAC TGGCCCTGCA ATACCTGTCC GAACACAGCT TCTCGGTCAG
4981 CCAGGGGGAC CGGGAGCAGG TACCTAACCT GGTCTACATG GTCACAGGAA ACCCCGCTTC
5041 TGATGAGATC AAGCGGATGC CTGGAGACAT CCAGGTGGTG CCCATCGGGG TGGGTCCACA
5101 TGCCAATGTG CAGGAGCTGG AGAAGATTGG CTGGCCCAAT GCCCCCATCC TCATCCATGA
5161 CTTTGAGATG CTCCCTCGAG AGGCTCCTGA TCTGGTGCTA CAGAGGTGCT GCTCTGGAGA
5221 GGGGCTGCAG ATCCCCACCC TCTCCCCCAC CCCAGATTGC AGCCAGCCCC TGGATGTGGT
5281 CCTCCTCCTG GATGGCTCTT CCAGCATTCC AGCTTCTTAC TTTGATGAAA TGAAGAGCTT
5341 CACCAAGGCT TTTATTTCAA GAGCTAATAT AGGGCCCCGG CTCACTCAAG TGTCGGTGCT
5401 GCAATATGGA AGCATCACCA CTATCGATGT GCCTTGGAAT GTAGCCTATG AGAAAGTCCA
5461 TTTACTGAGC CTTGTGGACC TCATGCAGCA GGAGGGAGGC CCCAGCGAAA TTGGGGATGC
5521 TTTGAGCTTT GCCGTGCGAT ATGTCACCTC AGAAGTCCAT GGTGCCAGGC CCGGAGCCTC
5581 GAAAGCGGTG GTTATCCTAG TCACAGATGT CTCCGTGGAT TCAGTGGATG CTGCAGCCGA
5641 GGCCGCCAGA TCCAACCGAG TGACAGTGTT CCCCATTGGA ATCGGGGATC GGTACAGTGA
5701 GGCCCAGCTG AGCAGCTTGG CAGGCCCAAA GGCTGGCTCC AATATGGTAA GGCTCCAGCG
5761 AATTGAAGAC CTCCCCACCG TGGCCACCCT GGGAAATTCC TTCTTCCACA AGCTGTGCTC
5821 TGGGTTTGAT AGAGTTTGCG TGGATGAGGA TGGGAATGAG AAGAGGCCCG GGATGTCTG
5881 GACCTTGCCA GACCAGTGCC ACACAGTGAC TTGCCTGCCA GATGGCCAGA CCTTGCTGAA
5941 GAGTCATCGG GTCAACTGTG ACCGGGGGCC AAGGCCTTCG TGCCCCAATG GCCAGCCCCC
6001 TCTCAGGGTA GAGGAGACCT GTGGCTGCCG CTGGACCTGT CCCTGTGTGT GCATGGGCAG
6061 CTCTACCCGG CACATCGTGA CCTTTGATGG GCAGAATTTC AAGCTGACTG GCAGCTGTTC
6121 GTATGTCCTA TTTCAAAACA AGGAGCAGGA CCTGGAGGTG ATTCTCCAGA ATGGTGCCTG
6181 CAGCCCTGGG GCGAAGGAGA CCTGCATGAA ATCCATTGAG GTGAAGCATG ACGGCCTCTC
6241 AGTTGAGCTC CACAGTGACA TGCAGATGAC AGTGAATGGG AGACTAGTCT CCATCCCATA
6301 TGTGGGTGGA GACATGGAAG TCAATGTTTA TGGGACCATC ATGTATGAGG TCAGATTCAA
6361 CCATCTTGGC CACATCTTCA CATTCACCCC CCAAAACAAT GAGTTCCAGC TGCAGCTCAG
```

FIGURE 1C

```
6421 CCCCAGGACC TTTGCTTCGA AGACATATGG TCTCTGTGGG ATCTGTGATG AGAACGGAGC
6481 CAATGACTTC ATTCTGAGGG ATGGGACAGT CACCCACAGAC TGGAAGGCAC TCATCCAGGA
6541 ATGGACCGTA CAGCAGCTTG GGAAGACATC CAGCCTGTC CATGAGGAGC AGTGTCCTGT
6601 CTCCGAATTC TTCCACTGCC AGGTCCTCCT CTCAGAATTG TTTGCCGAGT GCCACAAGGT
6661 CCTCGCTCCA GCCACCTTTT ATGCCATGTG CCAGCCCGAC AGTTGCCACC CGAAGAAAGT
6721 GTGTGAGGCG ATTGCCTTGT ATGCCCACCT CTGTCGGACC AAAGGGGTCT GTGTGGACTG
6781 GAGGAGGGCC AATTTCTGTG CTATGTCATG TCCACCATCC CTGGTGTACA ACCACTGTGA
6841 GCATGGCTGC CCTCGGCTCT GTGAAGGCAA TACAAGCTCC TGTGGGACC AACCCTCGGA
6901 AGGCTGCTTC TGCCCCCCAA ACCAAGTCAT GCTGGAAGGT AGCTGTGTCC CCGAGGAGGC
6961 CTGTACCCAG TGCATCAGCG AGGATGGAGT CCGGCACCAG TTCCTGGAAA CCTGGGTCCC
7021 AGCCCACCAG CCTTGCCAGA TCTGCACGTG CCTCAGTGGG CGGAAGGTCA ACTGTACGTT
7081 GCAGCCCTGC CCCACAGCCA AGCTCCCAC CTGTGGCCCG TGTAAGTGG CCCGCCTCCG
7141 CCAGAACGCA GTGCAGTGCT GCCCGGAGTA CGAGTGTGTG TGTGACCTGG TGAGCTGTGA
7201 CCTGCCCCCG GTGCCTCCCT GCGAAGATGG CCTCCAGATG ACCCTGACCA ATCCTGGCGA
7261 GTGCAGACCC AACTTCACCT GTGCCTGCAG GAAGGATGAA TGCAGACGGG AGTCCCCGCC
7321 CTCTTGTCCC CCGCACCGGA CGCCGGCCCT TCGGAAGACT CAGTGCTGTG ATGAGTATGA
7381 GTGTGCATGC AACTGTGTCA ACTCCACGGT GAGCTGCCCG CTTGGGTACC TGGCCTCGGC
7441 TGTCACCAAC GACTGTGGCT GCACCACAAC AACCTGCTTC CCTGACAAGG TGTGTGTCCA
7501 CCGAGGCACC ATCTACCCTG TGGGCCAGTT CTGGGAGGAG GCCTGTGACG TGTGCACCTG
7561 CACGGACTTG GAGGACTCTG TGATGGGCCT GCGTGTGGCC CAGTGCTCCC AGAAGCCCTG
7621 TGAGGACAAC TGCCTGTCAG GCTTCACTTA TGTCCTTCAT GAAGGCGAGT GCTGTGGAAG
7681 GTGTCTGCCA TCTGCCTGTG AGGTGGTCAC TGGTTCACCA CGGGGCGACG CCCAGTCTCA
7741 CTGGAAGAAT GTTGGCTCTC ACTGGGCCTC CCTGACAAC CCTGCCTCA TCAATGAGTG
7801 TGTCCGAGTG AAGGAAGAGG TCTTTGTGCA ACAGAGGAAT GTCTCCTGCC CCCAGCTGAA
7861 TGTCCCCACC TGCCCCACGG GCTTCCAGCT GAGCTGTAAG ACCTCAGAGT GTTGTCCCAC
7921 CTGTCACTGC GAGCCCTGG AGGCCTGCTT GCTCAATGGT ACCATCATTG GGCCGGGGAA
7981 AAGTCTGATG ATTGATGTGT GTACAACCTG CCGCTGCACC GTGCCGGTGG GAGTCATCTC
8041 TGGATTCAAG CTGGAGGCA GGAAGACCAC CTGTGAGGCA TGCCCCCTGG GTTATAAGGA
8101 AGAGAAGAAC CAAGGTGAAT GCTGTGGGAG ATGTCTGCCT ATAGCTTGCA CCATTCAGCT
8161 AAGAGGAGGA CAGATCATGA CACTGAAGCG TGATGAGACT ATCCAGGATG GCTGTGACAG
8221 TCACTTCTGC AAGGTCAATG AAAGAGGAGA GTACATCTGG GAGAAGAGAG TCACGGGTTG
8281 CCCACCTTTC GATGAACACA AGTGTCTGGC TGAGGGAGGA AAAATCATGA AAATTCCAGG
8341 CACCTGCTGT GACACATGTG AGGAGCCAGA ATGCAAGGAT ATCATTGCCA AGCTGCAGCG
8401 TGTCAAAGTG GGAGACTGTA AGTCTGAAGA GGAAGTGGAC ATTCATTACT GTGAGGGTAA
8461 ATGTGCCAGC AAAGCCGTGT ACTCCATCCA CATGGAGGAT GTGCAGGACC AGTGCTCCTG
8521 CTGCTCGCCC ACCCAGACGG AGCCCATGCA GGTGGCCCTG CGCTGCACCA ATGGCTCCCT
8581 CATCTACCAT GAGATCCTCA ATGCCATCGA ATGCAGGTGT CCCCCAGGA AGTGCAGCAA
8641 GTGAGGCCAC TGCCTGGATG CTACTGTCGC CTGCCTTACC CGACCTCACT GGACTGGCCA
8701 GAGTGCTGCT CAGTCCTCCT CAGTCCTCCT CCTGCTCTGC TCTTGTGCTT CCTGATCCCA
8761 CAATAAAGGT CAATCTTTCA CCTTGAAAAA AAAAAAAAA AA
```

```
Human  MIPARFAGVLLALALILPGTLCAEGTRGRSSTARCSLFGSDFVNTFDGSMYSFAGYCSYL      60
Dog    -S-T-LVR----------K--TK--V----M-----L-G--I----E-------D----

Human  LAGGCQKRSFSIIGDFQNGKRVSLSVYLGEFFDIHLFVNGTVTQGDQRVSMPYASKGLYL    120
Dog    ---D--EH-I-L--G---D--------------------ML--T-SI------N----

Human  ETEAGYYKLSGEAYGFVARIDGSGNFQVLLSDRYFNKTCGLCGNFNIFAEDDFMTQEGTL    180
Dog    -A--------S-----------N------------------------------K------

Human  TSDPYDFANSWALSSGEQWCERASPPSSSCNISSGEMQKGLWEQCQLLKSTSVFARCHPL    240
Dog    ----------------R-K-V-----P--V-D-V-QV----------A---------

Human  VDPEPFVALCEKTLCECAGGLECACPALLEYARTCAQEGMVLYGWTDHSACSPVCPAGME    300
Dog    -----------R---T-VQ-M--P-AV------A---Q-I---------V-R-A------

Human  YRQCVSPCARTCQSLHINEMCQERCVDGCSCPEGQLLDEGLCVESTECPCVHSGKRYPPG    360
Dog    -KE-----T-------VK-V---Q----------------H--G-A--S---A-Q-----

Human  TSLSRDCNTCICRNSQWICSNEECPGECLVTGQSHFKSFDNRYFTFSGICQYLLARDCQD    420
Dog    A--LQ--H------L------------------------------V-H----Q----

Human  HSFSIVIETVQCADDRDAVCTRSVTVRLPGLHNSLVKLKHGAGVAMDGQDVQLPLLKGDL    480
Dog    -T--V----------L---------------H--------N-G--S-----I-I---Q---

Human  RIQHTVTASVRLSYGEDLQMDWDGRGRLLVKLSPVYAGKTCGLCGNYNGNQGDDFLTPSG    540
Dog    ------M-------------S-V------T-Y-A-------RG------R----V--A-

Human  LAEPRVEDFGNAWKLHGDCQDLQKQHSDPCALNPRMTRFSEEACAVLTSPTFEACHRAVS    600
Dog    ----L----------L-A-EN-----R---S----QA--A-----L---SK--P-----G Human  PLPYLRNCRYDVCSCSDGRECLCGALASYAAACAGRGVRVAWREPGRCELNCPKGQVYLQ    660
Dog    -Q--VQ--L----------D---S-V-N----V-R---HI------F-A-S--Q------

Human  CGTPCNLTCRSLSYPDEECNEACLEGCFCPPGLYMDERGDCVPKAQCPCYYDGEIFQPED    720
Dog    ------M--L------E-D---V---S--S------L--|---|--------------

Human  IFSDHHTMCYCEDGFMHCTMSGVPGSLLPDAVLSSPLSHRSKRSLSCRPPMVKLVCPADN    780
Dog    ------------------T--GL-----NP-----RC---------------

Human  LRAEGLECTKTCQNYDLECMSMGCVSGCLPPGMVRHENRCVALERCPCFHQGKEYAPGE    840
Dog    P-------A---------Q---T--------Q----------------------Q------

Human  TVKIGCNTCVCRDRKWNCTDHVCDATCSTIGMAHYLTFDGLKYLFPGECQYVLVQDYCGS    900
Dog    ----D-----------T----------A------------------

Human  NPGTFRILVGNKGCSHPSVKCKKRVTILVEGGEIELFDGEVNVKRPMKDETHFEVVESGR    960
Dog    ----L------E---Y------------------K-------------Q Human  YIILLLGKALSVVWDRHLSISVVLKQTYQEKVCGLCGNFDGIQNNDLTSSNLQVEEDPVD   1020
Dog    -V-------------HR-----T--R----Q---------------F---S--I------

Human  FGNSWKVSSQCADTRKVPLDSSPATCHNNIMKQTMVDSSCRILTSDVFQDCNKLVDPEPY   1080
Dog    -------NP-----K---------V--------------------I-----R------F
```

FIGURE 2A

```
Human  LDVCIYDTCSCESIGDCACFCDTIAAYAHVCAQHGKVVTWRTATLCPQSCEERNLRENGY    1140
Dog    --I------------T--------------------A-----F---N------H----

Human  ECEWRYNSCAPACQVTCQHPEPLACPVQCVEGCHAHCPPGKILDELLQTCVDPEDCPVCE    1200
Dog    --------------PI-----------------------------------I--------

Human  VAGRRFASGKKVTLNPSDPEHCQICHCDVVNLTCEACQEPGGLVVPPTDAPVSPTTLYVE    1260
Dog    -----L-P---II------------N--G--F--K--R---SV------G-IGS--S---

Human  DISEPPLHDFYCSRLLDLVFLLDGSSRLSEAEFEVLKAFVVDMMERLRISQKWVRVAVVE    1320
Dog    -T--------H----------------K---D------V---G---H-H----RI------

Human  YHDGSHAYIGLKDRKRPSELRRIASQVKYAGSQVASTSEVLKYTLFQIFSKIDRPEASRI    1380
Dog    ----------E-------------T--------E----------------G----------

Human  ALLLMASQEPQRMSRNFVRYVQGLKKKKVIVIPVGIGPHANLKQIRLIEKQAPENKAFVL    1440
Dog    ----------S-LA--L----------------------S----H------------F Human  SSVDELEQQRDEIVSYLCDLAPEAPPPTLPPHMAQVTVGPGLLGVSTLGPKRNSMVLDVA    1500
Dog    -G------R----IN-----------A--QH-P-------SE-----SP----------V Human  FVLEGSDKIGEADFNRSKEFMEEVIQRMDVGQDSIHVTVLQYSYMVTVEYPFSEAQSKGD    1560
Dog    -------------N--K-R--------------R---------------T--------E Human  ILQRVREIRYQGGNRTNTGLALRYLSDHSFLVSQGDREQAPNLVYMVTGNPASDEIKRLP    1620
Dog    V--Q--D---R-----------Q---E---S--------V----------------M-

Human  GDIQVVPIGVGPNANVQELERIGWPNAPILIQDFETLPREAPDLVLQRCCSGEGLCIPTL    1680
Dog    -------------H-------K----------H---M----------------------

Human  SPAPDCSQPLDVILLLDGSSSFPASYFDEMKSFAKAFISKANIGPRLTQVSVLQYGSITT    1740
Dog    --T----------V--------I------------T-----R-----------------

Human  IDVPWNVVPEKAHLLSLVDVMQREGGPSQIGDALGFAVRYLTSEMHGARPGASKAVVILV    1800
Dog    -------AY--V--------L--Q-----E-----S-----V---V-------------

Human  TDVSVDSVDAAADAARSNRVTVFPIGIGDRYDAAQLRILAGPAGDSNVVKLQRIEDLPTM    1860
Dog    -------------E-----------------SE---SS----KAG--M-R---------V Human  VTLGNSFLHKLCSGFVRICMDEDGNEKRPGDVWTLPDQCHTVTCQPDGQTLLKTHRVNCD    1920
Dog    A------F--------D-V-V--------------------------L--------S------

Human  RGLRPSCPNSQSPVKVEETCGCRWTCPCVCTGSSTRHIVTFDGQNFKLTGSCSYVLFQNK    1980
Dog    --P------G-P-LR---------------M-----------------------------

Human  EQDLEVILHNGACSPGARQGCMKSIEVKHSALSVELHSDMEVTVNGRLVSVPYVGGNMEV    2040
Dog    --------Q---------KET---------DG---------QM--------I-----D---

Human  NVYGAIMHEVRFNHLGHIFTFTPQNNEFQLQLSPKTFASKTYGLCGICDENGANDFMLRD    2100
Dog    ----T--Y---------------------------R------------------I---

Human  GTVTTDWKTLVQEWTVQRPGQTCQPILEEQCLVPDSSHCQVLLLPLFAECHKVLAPATFY    2160
Dog    --------A-I------QL-K-S--VH----P-SEFF------SE--------------
```

FIGURE 2B

```
Human   AICQQDSCHQEQVCEVIASYAHLCRTNGVCVDWRTPDFCAMSCPPSLVYNHCEHGCPRHC    2220
Dog     -M--P----PKK---A--L-------K-------RAN--------------------L-

Human   DGNVSSCGDHPSEGCFCPPDKVMLEGSCVPEEACTQCIGEDGVQHQFLEAWVPDHQPCQI    2280
Dog     E--T-----Q---------NQ----------------S----R-----T---A------

Human   CTCLSGRKVNCTTQPCPTAKAPTCGLCEVARLRQNADQCCPEYECVCDPVSCDLPPVPHC    2340
Dog     -------------L------------P----------V-----------L---------P-

Human   ERGLQPTLTNPGECRPNFTCACRKEECKRVSPPSCPPHRLPTLRKTQCCDEYECACNCVN    2400
Dog     -D---M----------------D--R-E---------T-A------------------

Human   STVSCPLGYLASTATNDCGCTTTTCLPDKVCVHRSTIYPVGQFWEEGCDVCTCTDMEDAV    2460
Dog     ------------AV----------F--------G-----------A-------L--S-

Human   MGLRVAQCSQKPCEDSCRSGFTYVLHEGECCGRCLPSACEVVTGSRGDSQSSWKSVGSQ    2520
Dog     ---------------N-L--------------------------------A--H--N---H Human   WASPENPCLINECVRVKEEVFIQQRNVSCPQLEVPVCPSGFQLSCKTSACCPSCRCERME    2580
Dog     ----D----------------V----------N--T--T---------E---T-H--PL- Human   ACMLNGTVIGPGKTVMIDVCTTCRCMVQVGVISGFKLECRKTTCNPCPLGYKEENNTGEC    2640
Dog     --L----I-----SL-----------T-P----------G-----EA--------K-Q---

Human   CGRCLPTACTIQLRGGQIMTLKRDETLQDGCDTHFCKVNERGEYFWEKRVTGCPPFDEHK    2700
Dog     ------I------------------I-----S----------I----------------

Human   CLAEGGKIMKIPGTCCDTCEEPECNDITARLQYVKVGSCKSEVEVDIHYCQGKCASKAMY    2760
Dog     -----------------------K--I-K--R----D----E-------E-------V-

Human   SIDINDVQDQCSCCSPTRTEPMQVALHCTNGSVVYHEVLNAMECKCSPRKCSK    2813
Dog     --HME------------Q--------R-----LI---I---I--R--------
```

FIGURE 2C

```
exon 4      AAATGACAAAAGAGTGAGCCGGTC*
AGGGGGTTTCCAAAATGACAAAAGAGTGAGCCTCTCCGTGTATCTCGGAGAATTTTTCGA
   G  G  F  Q  N  D  K  R  V  S  L  S  V  Y  L  G  E  F  F  D CATTCATTTGTTTGTCAATGGTACCATGCTGCAGGGGACCCAAAGGTAAGTCAGAAGCCC
   I  H  L  F  V  N  G  T  M  L  Q  G  T  Q  R

GAATGTTCAGGTTAATATGGACCCTGGGGATCACTTTGCAACCCCCTTGTTTTTTCAGAT

GAGGGAGCCGGGGCCCAGAGACAGGAAGTAAATGTGCCCAGGGAAAGTGAGTGGCAGGAC

TGGGTGAAAGCCCCATATCCCGACTCCTGGTCAAGGAGACTTTGCACCAAGGTCCCAGCC
              3'-GGGCTGGCGACCAGTTCCTCTGAA-5'

CTGGAGCATGGGGTTGGGGTTGGAAGGTGGAGGGACATGGAGGAAATGCATGAGAAGCAC
                              exon 5
GCTTCCTGAGCTCCTCCTTGTCCCACCAGCATCTCCATGCCCTACGCCTCCAATGGGC
                               I  S  M  P  Y  A  S  N  G
```

FIGURE 4

```
                              SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 8802 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 203..8641
        (D) OTHER INFORMATION: /function= "Blood Clotting Protein"
            /product= "Canine von Willebrand Factor"
            /standard_name= "vWF"

(x) PUBLICATION INFORMATION:
        (A) AUTHORS: Venta, Patrick J.
            Li, Jianping
            Yuzbasiyan-Gurkan, Vilma
            Schall, William D.
            Brewer, George J.
        (B) TITLE: Von Willebrand's Disease in the Scottish
            Terrier is Caused by a Single Base Deletion in
            Exon Four of the von Willebrand Factor Gene
        (C) JOURNAL: Journal of the American Veterinary Medicine
                    Association
        (G) DATE: 1996
        (K) RELEVANT RESIDUES IN SEQ ID NO:1: FROM 1 TO 8802

(xi) SEQUENCE DESCRIPTION: SEQ ID NO:1:

CATTAAAAGG TCCTGGCTGG GAGCTTTTTT TTGGGACCAG CACTCCATGT TCAAGGGCAA      60

ACAGGGGCCA ATTAGGATCA ATCTTTTTTC TTTCTTTTTT TAAAAAAAAA AATTCTTCCC     120

ACTTTGCACA CGGACAGTAG TACATACCAG TAGCTCTCTG CGAGGACGGT GATCACTAAT     180

CATTTCTCCT GCTTCGTGGC AG ATG AGT CCT ACC AGA CTT GTG AGG GTG CTG     232
                         Met Ser Pro Thr Arg Leu Val Arg Val Leu
                           1               5                  10

CTG GCT CTG GCC CTC ATC TTG CCA GGG AAA CTT TGT ACA AAA GGG ACT     280
Leu Ala Leu Ala Leu Ile Leu Pro Gly Lys Leu Cys Thr Lys Gly Thr
             15                  20                  25
```

```
GTT GGA AGG TCA TCG ATG GCC CGA TGT AGC CTT CTC GGA GGT GAC TTC      328
Val Gly Arg Ser Ser Met Ala Arg Cys Ser Leu Leu Gly Gly Asp Phe
            30              35              40

ATC AAC ACC TTT GAT GAG AGC ATG TAC AGC TTT GCG GGA GAT TGC AGT      376
Ile Asn Thr Phe Asp Glu Ser Met Tyr Ser Phe Ala Gly Asp Cys Ser
            45              50              55

TAC CTC CTG GCT GGG GAC TGC CAG GAA CAC TCC ATC TCA CTT ATC GGG      424
Tyr Leu Leu Ala Gly Asp Cys Gln Glu His Ser Ile Ser Leu Ile Gly
    60              65              70

GGT TTC CAA AAT GAC AAA AGA GTG AGC CTC TCC GTG TAT CTC GGA GAA      472
Gly Phe Gln Asn Asp Lys Arg Val Ser Leu Ser Val Tyr Leu Gly Glu
    75              80              85              90

TTT TTC GAC ATT CAT TTG TTT GTC AAT GGT ACC ATG CTG CAG GGG ACC      520
Phe Phe Asp Ile His Leu Phe Val Asn Gly Thr Met Leu Gln Gly Thr
                95              100             105

CAA AGC ATC TCC ATG CCC TAC GCC TCC AAT GGG CTG TAT CTA GAG GCC      568
Gln Ser Ile Ser Met Pro Tyr Ala Ser Asn Gly Leu Tyr Leu Glu Ala
            110             115             120

GAG GCT GGC TAC TAC AAG CTG TCC AGT GAG GCC TAC GGC TTT GTG GCC      616
Glu Ala Gly Tyr Tyr Lys Leu Ser Ser Glu Ala Tyr Gly Phe Val Ala
            125             130             135

AGA ATT GAT GGC AAT GGC AAC TTT CAA GTC CTG CTG TCA GAC AGA TAC      664
Arg Ile Asp Gly Asn Gly Asn Phe Gln Val Leu Leu Ser Asp Arg Tyr
    140             145             150

TTC AAC AAG ACC TGT GGG CTG TGT GGC AAC TTT AAT ATC TTT GCT GAG      712
Phe Asn Lys Thr Cys Gly Leu Cys Gly Asn Phe Asn Ile Phe Ala Glu
155             160             165             170

GAT GAC TTC AAG ACT CAA GAA GGG ACG TTG ACT TCG GAC CCC TAT GAC      760
Asp Asp Phe Lys Thr Gln Glu Gly Thr Leu Thr Ser Asp Pro Tyr Asp
            175             180             185

TTT GCC AAC TCC TGG GCC CTG AGC AGT GGG GAA CAA CGG TGC AAA CGG      808
Phe Ala Asn Ser Trp Ala Leu Ser Ser Gly Glu Gln Arg Cys Lys Arg
            190             195             200

GTG TCC CCT CCC AGC AGC CCA TGC AAT GTC TCC TCT GAT GAA GTG CAG      856
Val Ser Pro Pro Ser Ser Pro Cys Asn Val Ser Ser Asp Glu Val Gln
            205             210             215

CAG GTC CTG TGG GAG CAG TGC CAG CTC CTG AAG AGT GCC TCG GTG TTT      904
Gln Val Leu Trp Glu Gln Cys Gln Leu Leu Lys Ser Ala Ser Val Phe
            220             225             230

GCC CGC TGC CAC CCG CTG GTG GAC CCT GAG CCT TTT GTC GCC CTG TGT      952
Ala Arg Cys His Pro Leu Val Asp Pro Glu Pro Phe Val Ala Leu Cys
235             240             245             250

GAA AGG ACT CTG TGC ACC TGT GTC CAG GGG ATG GAG TGC CCT TGT GCG      1000
Glu Arg Thr Leu Cys Thr Cys Val Gln Gly Met Glu Cys Pro Cys Ala
            255             260             265

GTC CTC CTG GAG TAC GCC CGG GCC TGT GCC CAG CAG GGG ATT GTC TTG      1048
Val Leu Leu Glu Tyr Ala Arg Ala Cys Ala Gln Gln Gly Ile Val Leu
            270             275             280

TAC GGC TGG ACC GAC CAC AGC GTC TGC CGA CCA GCA TGC CCT GCT GGC      1096
Tyr Gly Trp Thr Asp His Ser Val Cys Arg Pro Ala Cys Pro Ala Gly
            285             290             295

ATG GAG TAC AAG GAG TGC GTG TCC CCT TGC ACC AGA ACT TGC AGC AGC      1144
Met Glu Tyr Lys Glu Cys Val Ser Pro Cys Thr Arg Thr Cys Gln Ser
            300             305             310

CTT CAT GTC AAA GAA GTG TGT CAG GAG CAA TGT GTA GAT GGC TGC AGC      1192
Leu His Val Lys Glu Val Cys Gln Glu Gln Cys Val Asp Gly Cys Ser
315             320             325             330

TGC CCC GAG GGC CAG CTC CTG GAT GAA GGC CAC TGC GTG GGA AGT GCT      1240
Cys Pro Glu Gly Gln Leu Leu Asp Glu Gly His Cys Val Gly Ser Ala
            335             340             345
```

```
GAG TGT TCC TGT GTG CAT GCT GGG CAA CGG TAC CCT CCG GGC GCC TCC    1288
Glu Cys Ser Cys Val His Ala Gly Gln Arg Tyr Pro Pro Gly Ala Ser
            350                 355                 360

CTC TTA CAG GAC TGC CAC ACC TGC ATT TGC CGA AAT AGC CTG TGG ATC    1336
Leu Leu Gln Asp Cys His Thr Cys Ile Cys Arg Asn Ser Leu Trp Ile
        365                 370                 375

TGC AGC AAT GAA GAA TGC CCA GGC GAG TGT CTG GTC ACA GGA CAG TCC    1384
Cys Ser Asn Glu Glu Cys Pro Gly Glu Cys Leu Val Thr Gly Gln Ser
    380                 385                 390

CAC TTC AAG AGC TTC GAC AAC AGG TAC TTC ACC TTC AGT GGG GTC TGC    1432
His Phe Lys Ser Phe Asp Asn Arg Tyr Phe Thr Phe Ser Gly Val Cys
395                 400                 405                 410

CAC TAC CTG CTG GCC CAG GAC TGC CAG GAC CAC ACA TTC TCT GTT GTC    1480
His Tyr Leu Leu Ala Gln Asp Cys Gln Asp His Thr Phe Ser Val Val
                415                 420                 425

ATA GAG ACT GTC CAG TGT GCC GAT GAC CTG GAT GCT GTC TGC ACC CGC    1528
Ile Glu Thr Val Gln Cys Ala Asp Asp Leu Asp Ala Val Cys Thr Arg
            430                 435                 440

TCG GTC ACC GTC CGC CTG CCT GGA CAT CAC AAC AGC CTT GTG AAG CTG    1576
Ser Val Thr Val Arg Leu Pro Gly His His Asn Ser Leu Val Lys Leu
        445                 450                 455

AAG AAT GGG GGA GGA GTC TCC ATG GAT GGC CAG GAT ATC CAG ATT CCT    1624
Lys Asn Gly Gly Gly Val Ser Met Asp Gly Gln Asp Ile Gln Ile Pro
    460                 465                 470

CTC CTG CAA GGT GAC CTC CGC ATC CAG CAC ACC GTG ATG GCC TCC GTG    1672
Leu Leu Gln Gly Asp Leu Arg Ile Gln His Thr Val Met Ala Ser Val
475                 480                 485                 490

CGC CTC AGC TAC GGG GAG GAC CTG CAG ATG GAT TCG GAC GTC CGG GGC    1720
Arg Leu Ser Tyr Gly Glu Asp Leu Gln Met Asp Ser Asp Val Arg Gly
                495                 500                 505

AGG CTA CTG GTG ACG CTG TAC CCC GCC TAC GCG GGG AAG ACG TGC GGC    1768
Arg Leu Leu Val Thr Leu Tyr Pro Ala Tyr Ala Gly Lys Thr Cys Gly
            510                 515                 520

CGT GGC GGG AAC TAC AAC GGC AAC CGG GGG GAC GAC TTC GTG ACG CCC    1816
Arg Gly Gly Asn Tyr Asn Gly Asn Arg Gly Asp Asp Phe Val Thr Pro
        525                 530                 535

GCA GGC CTG GCG GAG CCC CTG GTG GAG GAC TTC GGG AAC GCC TGG AAG    1864
Ala Gly Leu Ala Glu Pro Leu Val Glu Asp Phe Gly Asn Ala Trp Lys
    540                 545                 550

CTG CTC GGG GCC TGC GAG AAC CTG CAG AAG CAG CAC CGC GAT CCC TGC    1912
Leu Leu Gly Ala Cys Glu Asn Leu Gln Lys Gln His Arg Asp Pro Cys
555                 560                 565                 570

AGC CTC AAC CCG CGC CAG GCC AGG TTT GCG GAG GAG GCG TGC GCG CTG    1960
Ser Leu Asn Pro Arg Gln Ala Arg Phe Ala Glu Glu Ala Cys Ala Leu
                575                 580                 585

CTG ACG TCC TCG AAG TTC GAG CCC TGC CAC CGA GCG GTG GGT CCT CAG    2008
Leu Thr Ser Ser Lys Phe Glu Pro Cys His Arg Ala Val Gly Pro Gln
            590                 595                 600

CCC TAC GTG CAG AAC TGC CTC TAC GAC GTC TGC TCC TGC TCC GAC GGC    2056
Pro Tyr Val Gln Asn Cys Leu Tyr Asp Val Cys Ser Cys Ser Asp Gly
        605                 610                 615

AGA GAC TGT CTT TGC AGC GCC GTG GCC AAC TAC GCC GCA GCC GTG GCC    2104
Arg Asp Cys Leu Cys Ser Ala Val Ala Asn Tyr Ala Ala Ala Val Ala
    620                 625                 630

CGG AGG GGC GTG CAC ATC GCG TGG CGG GAG CCG GGC TTC TGT GCG CTG    2152
Arg Arg Gly Val His Ile Ala Trp Arg Glu Pro Gly Phe Cys Ala Leu
635                 640                 645                 650

AGC TGC CCC CAG GGC CAG GTG TAC CTG CAG TGT GGG ACC CCC TGC AAC    2200
Ser Cys Pro Gln Gly Gln Val Tyr Leu Gln Cys Gly Thr Pro Cys Asn
```

```
                    655                 660                 665
ATG ACC TGT CTC TCC CTC TCT TAC CCG GAG GAG GAC TGC AAT GAG GTC       2248
Met Thr Cys Leu Ser Leu Ser Tyr Pro Glu Glu Asp Cys Asn Glu Val
            670                 675                 680

TGC TTG GAA AGC TGC TTC TCC CCC CCA GGG CTG TAC CTG GAT GAG AGG       2296
Cys Leu Glu Ser Cys Phe Ser Pro Pro Gly Leu Tyr Leu Asp Glu Arg
            685                 690                 695

GGA GAT TGT GTG CCC AAG GCT CAG TGT CCC TGT TAC TAT GAT GGT GAG       2344
Gly Asp Cys Val Pro Lys Ala Gln Cys Pro Cys Tyr Tyr Asp Gly Glu
    700                 705                 710

ATC TTT CAG CCC GAA GAC ATC TTC TCA GAC CAT CAC ACC ATG TGC TAC       2392
Ile Phe Gln Pro Glu Asp Ile Phe Ser Asp His His Thr Met Cys Tyr
715                 720                 725                 730

TGT GAG GAT GGC TTC ATG CAC TGT ACC ACA AGT GGA GGC CTG GGA AGC       2440
Cys Glu Asp Gly Phe Met His Cys Thr Thr Ser Gly Gly Leu Gly Ser
                735                 740                 745

CTG CTG CCC AAC CCG GTG CTC AGC AGC CCC CGG TGT CAC CGC AGC AAA       2488
Leu Leu Pro Asn Pro Val Leu Ser Ser Pro Arg Cys His Arg Ser Lys
            750                 755                 760

AGG AGC CTG TCC TGT CGG CCC CCC ATG GTC AAG TTG GTG TGT CCC GCT       2536
Arg Ser Leu Ser Cys Arg Pro Pro Met Val Lys Leu Val Cys Pro Ala
            765                 770                 775

GAT AAC CCG AGG GCT GAA GGA CTG GAG TGT GCC AAA ACC TGC CAG AAC       2584
Asp Asn Pro Arg Ala Glu Gly Leu Glu Cys Ala Lys Thr Cys Gln Asn
780                 785                 790

TAT GAC CTG CAG TGC ATG AGC ACA GGC TGT GTC TCC GGC TGC CTC TGC       2632
Tyr Asp Leu Gln Cys Met Ser Thr Gly Cys Val Ser Gly Cys Leu Cys
795                 800                 805                 810

CCG CAG GGC ATG GTC CGG CAT GAA AAC AGG TGT GTG GCG CTG GAA AGA       2680
Pro Gln Gly Met Val Arg His Glu Asn Arg Cys Val Ala Leu Glu Arg
                815                 820                 825

TGT CCC TGC TTC CAC CAA GGC CAA GAG TAC GCC CCA GGA GAA ACC GTG       2728
Cys Pro Cys Phe His Gln Gly Gln Glu Tyr Ala Pro Gly Glu Thr Val
            830                 835                 840

AAA ATT GAC TGC AAC ACT TGT GTC TGT CGG GAC CGG AAG TGG ACC TGC       2776
Lys Ile Asp Cys Asn Thr Cys Val Cys Arg Asp Arg Lys Trp Thr Cys
            845                 850                 855

ACA GAC CAT GTG TGT GAT GCC ACT TGC TCT GCC ATC GGC ATG GCG CAC       2824
Thr Asp His Val Cys Asp Ala Thr Cys Ser Ala Ile Gly Met Ala His
            860                 865                 870

TAC CTC ACC TTC GAC GGA CTC AAG TAC CTG TTC CCT GGG GAG TGC CAG       2872
Tyr Leu Thr Phe Asp Gly Leu Lys Tyr Leu Phe Pro Gly Glu Cys Gln
875                 880                 885                 890

TAT GTT CTG GTG CAG GAT TAC TGC GGC AGT AAC CCT GGG ACC TTA CGG       2920
Tyr Val Leu Val Gln Asp Tyr Cys Gly Ser Asn Pro Gly Thr Leu Arg
                895                 900                 905

ATC CTG GTG GGG AAC GAG GGG TGC AGC TAC CCC TCA GTG AAA TGC AAG       2968
Ile Leu Val Gly Asn Glu Gly Cys Ser Tyr Pro Ser Val Lys Cys Lys
            910                 915                 920

AAG CGG GTC ACC ATC CTG GTG GAA GGA GGA GAG ATT GAA CTG TTT GAT       3016
Lys Arg Val Thr Ile Leu Val Glu Gly Gly Glu Ile Glu Leu Phe Asp
            925                 930                 935

GGG GAG GTG AAT GTG AAG AAA CCC ATG AAG GAT GAG ACT CAC TTT GAG       3064
Gly Glu Val Asn Val Lys Lys Pro Met Lys Asp Glu Thr His Phe Glu
            940                 945                 950

GTG GTA GAG TCT GGT CAG TAC GTC ATT CTG CTG CTG GGC AAG GCA CTC       3112
Val Val Glu Ser Gly Gln Tyr Val Ile Leu Leu Leu Gly Lys Ala Leu
955                 960                 965                 970

TCT GTG GTC TGG GAC CAC CGC CTG AGC ATC TCT GTG ACC CTG AAG CGG       3160
```

-continued

```
Ser Val Val Trp Asp His Arg Leu Ser Ile Ser Val Thr Leu Lys Arg
                975                 980                 985

ACA TAC CAG GAG CAG GTG TGT GGC CTG TGT GGG AAT TTT GAT GGC ATC         3208
Thr Tyr Gln Glu Gln Val Cys Gly Leu Cys Gly Asn Phe Asp Gly Ile
            990                 995                 1000

CAG AAC AAT GAT TTC ACC AGC AGC AGC CTC CAA ATA GAA GAA GAC CCT         3256
Gln Asn Asn Asp Phe Thr Ser Ser Ser Leu Gln Ile Glu Glu Asp Pro
        1005                1010                1015

GTG GAC TTT GGG AAT TCC TGG AAA GTG AAC CCG CAG TGT GCC GAC ACC         3304
Val Asp Phe Gly Asn Ser Trp Lys Val Asn Pro Gln Cys Ala Asp Thr
    1020                1025                1030

AAG AAA GTA CCA CTG GAC TCA TCC CCT GCC GTC TGC CAC AAC AAC ATC         3352
Lys Lys Val Pro Leu Asp Ser Ser Pro Ala Val Cys His Asn Asn Ile
1035                1040                1045                1050

ATG AAG CAG ACG ATG GTG GAT TCC TCC TGC AGG ATC CTC ACC AGT GAT         3400
Met Lys Gln Thr Met Val Asp Ser Ser Cys Arg Ile Leu Thr Ser Asp
                1055                1060                1065

ATT TTC CAG GAC TGC AAC AGG CTG GTG GAC CCT GAG CCA TTC CTG GAC         3448
Ile Phe Gln Asp Cys Asn Arg Leu Val Asp Pro Glu Pro Phe Leu Asp
            1070                1075                1080

ATT TGC ATC TAC GAC ACT TGC TCC TGT GAG TCC ATT GGG GAC TGC ACC         3496
Ile Cys Ile Tyr Asp Thr Cys Ser Cys Glu Ser Ile Gly Asp Cys Thr
        1085                1090                1095

TGC TTC TGT GAC ACC ATT GCT GCT TAC GCC CAC GTC TGT GCC CAG CAT         3544
Cys Phe Cys Asp Thr Ile Ala Ala Tyr Ala His Val Cys Ala Gln His
    1100                1105                1110

GGC AAG GTG GTA GCC TGG AGG ACA GCC ACA TTC TGT CCC CAG AAT TGC         3592
Gly Lys Val Val Ala Trp Arg Thr Ala Thr Phe Cys Pro Gln Asn Cys
1115                1120                1125                1130

GAG GAG CGG AAT CTC CAC GAG AAT GGG TAT GAG TGT GAG TGG CGC TAT         3640
Glu Glu Arg Asn Leu His Glu Asn Gly Tyr Glu Cys Glu Trp Arg Tyr
                1135                1140                1145

AAC AGC TGT GCC CCT GCC TGT CCC ATC ACG TGC CAG CAC CCC GAG CCA         3688
Asn Ser Cys Ala Pro Ala Cys Pro Ile Thr Cys Gln His Pro Glu Pro
            1150                1155                1160

CTG GCA TGC CCT GTA CAG TGT GTT GAA GGT TGC CAT GCG CAC TGC CCT         3736
Leu Ala Cys Pro Val Gln Cys Val Glu Gly Cys His Ala His Cys Pro
        1165                1170                1175

CCA GGG AAA ATC CTG GAT GAG CTT TTG CAG ACC TGC ATC GAC CCT GAA         3784
Pro Gly Lys Ile Leu Asp Glu Leu Leu Gln Thr Cys Ile Asp Pro Glu
    1180                1185                1190

GAC TGT CCT GTG TGT GAG GTG GCT GGT CGT CGC TTG GCC CCA GGA AAG         3832
Asp Cys Pro Val Cys Glu Val Ala Gly Arg Arg Leu Ala Pro Gly Lys
1195                1200                1205                1210

AAA ATC ATC TTG AAC CCC AGT GAC CCT GAG CAC TGC CAA ATT TGT AAT         3880
Lys Ile Ile Leu Asn Pro Ser Asp Pro Glu His Cys Gln Ile Cys Asn
                1215                1220                1225

TGT GAT GGT GTC AAC TTC ACC TGT AAG GCC TGC AGA GAA CCC GGA AGT         3928
Cys Asp Gly Val Asn Phe Thr Cys Lys Ala Cys Arg Glu Pro Gly Ser
            1230                1235                1240

GTT GTG GTG CCC CCC ACA GAT GGC CCC ATT GGC TCT ACC ACC TCG TAT         3976
Val Val Val Pro Pro Thr Asp Gly Pro Ile Gly Ser Thr Thr Ser Tyr
        1245                1250                1255

GTG GAG GAC ACG TCG GAG CCG CCC CTC CAT GAC TTC CAC TGC AGC AGG         4024
Val Glu Asp Thr Ser Glu Pro Pro Leu His Asp Phe His Cys Ser Arg
    1260                1265                1270

CTT CTG GAC CTG GTT TTC CTG CTG GAT GGC TCC TCC AAG CTG TCT GAG         4072
Leu Leu Asp Leu Val Phe Leu Leu Asp Gly Ser Ser Lys Leu Ser Glu
1275                1280                1285                1290
```

```
GAC GAG TTT GAA GTG CTG AAG GTC TTT GTG GTG GGT ATG ATG GAG CAT    4120
Asp Glu Phe Glu Val Leu Lys Val Phe Val Val Gly Met Met Glu His
                1295            1300            1305

CTG CAC ATC TCC CAG AAG CGG ATC CGC GTG GCT GTG GTG GAG TAC CAC    4168
Leu His Ile Ser Gln Lys Arg Ile Arg Val Ala Val Val Glu Tyr His
            1310            1315            1320

GAC GGC TCC CAC GCC TAC ATC GAG CTC AAG GAC CGG AAG CGA CCC TCA    4216
Asp Gly Ser His Ala Tyr Ile Glu Leu Lys Asp Arg Lys Arg Pro Ser
        1325            1330            1335

GAG CTG CGG CGC ATC ACC AGC CAG GTG AAG TAC GCG GGC AGC GAG GTG    4264
Glu Leu Arg Arg Ile Thr Ser Gln Val Lys Tyr Ala Gly Ser Glu Val
    1340            1345            1350

GCC TCC ACC AGT GAG GTC TTA AAG TAC ACG CTG TTC CAG ATC TTT GGC    4312
Ala Ser Thr Ser Glu Val Leu Lys Tyr Thr Leu Phe Gln Ile Phe Gly
1355            1360            1365            1370

AAG ATC GAC CGC CCG GAA GCG TCT CGC ATT GCC CTG CTC CTG ATG GCC    4360
Lys Ile Asp Arg Pro Glu Ala Ser Arg Ile Ala Leu Leu Leu Met Ala
                1375            1380            1385

AGC CAG GAG CCC TCA AGG CTG GCC CGG AAT TTG GTC CGC TAT GTG CAG    4408
Ser Gln Glu Pro Ser Arg Leu Ala Arg Asn Leu Val Arg Tyr Val Gln
            1390            1395            1400

GGC CTG AAG AAG AAG AAA GTC ATT GTC ATC CCT GTG GGC ATC GGG CCC    4456
Gly Leu Lys Lys Lys Lys Val Ile Val Ile Pro Val Gly Ile Gly Pro
        1405            1410            1415

CAC GCC AGC CTT AAG CAG ATC CAC CTC ATA GAG AAG CAG GCC CCT GAG    4504
His Ala Ser Leu Lys Gln Ile His Leu Ile Glu Lys Gln Ala Pro Glu
    1420            1425            1430

AAC AAG GCC TTT GTG TTC AGT GGT GTG GAT GAG TTG GAG CAG CGA AGG    4552
Asn Lys Ala Phe Val Phe Ser Gly Val Asp Glu Leu Glu Gln Arg Arg
1435            1440            1445            1450

GAT GAG ATT ATC AAC TAC CTC TGT GAC CTT GCC CCC GAA GCA CCT GCC    4600
Asp Glu Ile Ile Asn Tyr Leu Cys Asp Leu Ala Pro Glu Ala Pro Ala
                1455            1460            1465

CCT ACT CAG CAC CCC CCA ATG GCC CAG GTC ACG GTG GGT TCG GAG CTG    4648
Pro Thr Gln His Pro Pro Met Ala Gln Val Thr Val Gly Ser Glu Leu
            1470            1475            1480

TTG GGG GTT TCA TCT CCA GGA CCC AAA AGG AAC TCC ATG GTC CTG GAT    4696
Leu Gly Val Ser Ser Pro Gly Pro Lys Arg Asn Ser Met Val Leu Asp
        1485            1490            1495

GTG GTG TTT GTC CTG GAA GGG TCA GAC AAA ATT GGT GAG GCC AAC TTT    4744
Val Val Phe Val Leu Glu Gly Ser Asp Lys Ile Gly Glu Ala Asn Phe
    1500            1505            1510

AAC AAA AGC AGG GAG TTC ATG GAG GAG GTG ATT CAG CGG ATG GAC GTG    4792
Asn Lys Ser Arg Glu Phe Met Glu Glu Val Ile Gln Arg Met Asp Val
1515            1520            1525            1530

GGC CAG GAC AGG ATC CAC GTC ACA GTG CTG CAG TAC TCG TAC ATG GTG    4840
Gly Gln Asp Arg Ile His Val Thr Val Leu Gln Tyr Ser Tyr Met Val
                1535            1540            1545

ACC GTG GAG TAC ACC TTC AGC GAG GCG CAG TCC AAG GGC GAG GTC CTA    4888
Thr Val Glu Tyr Thr Phe Ser Glu Ala Gln Ser Lys Gly Glu Val Leu
            1550            1555            1560

CAG CAG GTG CGG GAT ATC CGA TAC CGG GGT GGC AAC AGG ACC AAC ACT    4936
Gln Gln Val Arg Asp Ile Arg Tyr Arg Gly Gly Asn Arg Thr Asn Thr
        1565            1570            1575

GGA CTG GCC CTG CAA TAC CTG TCC GAA CAC AGC TTC TCG GTC AGC CAG    4984
Gly Leu Ala Leu Gln Tyr Leu Ser Glu His Ser Phe Ser Val Ser Gln
    1580            1585            1590

GGG GAC CGG GAG CAG GTA CCT AAC CTG GTC TAC ATG GTC ACA GGA AAC    5032
Gly Asp Arg Glu Gln Val Pro Asn Leu Val Tyr Met Val Thr Gly Asn
1595            1600            1605            1610
```

```
CCC GCT TCT GAT GAG ATC AAG CGG ATG CCT GGA GAC ATC CAG GTG GTG         5080
Pro Ala Ser Asp Glu Ile Lys Arg Met Pro Gly Asp Ile Gln Val Val
                1615                1620                1625

CCC ATC GGG GTG GGT CCA CAT GCC AAT GTG CAG GAG CTG GAG AAG ATT         5128
Pro Ile Gly Val Gly Pro His Ala Asn Val Gln Glu Leu Glu Lys Ile
                1630                1635                1640

GGC TGG CCC AAT GCC CCC ATC CTC ATC CAT GAC TTT GAG ATG CTC CCT         5176
Gly Trp Pro Asn Ala Pro Ile Leu Ile His Asp Phe Glu Met Leu Pro
                1645                1650                1655

CGA GAG GCT CCT GAT CTG GTG CTA CAG AGG TGC TGC TCT GGA GAG GGG         5224
Arg Glu Ala Pro Asp Leu Val Leu Gln Arg Cys Cys Ser Gly Glu Gly
                1660                1665                1670

CTG CAG ATC CCC ACC CTC TCC CCC ACC CCA GAT TGC AGC CAG CCC CTG         5272
Leu Gln Ile Pro Thr Leu Ser Pro Thr Pro Asp Cys Ser Gln Pro Leu
1675                1680                1685                1690

GAT GTG GTC CTC CTC CTG GAT GGC TCT TCC AGC ATT CCA GCT TCT TAC         5320
Asp Val Val Leu Leu Leu Asp Gly Ser Ser Ser Ile Pro Ala Ser Tyr
                1695                1700                1705

TTT GAT GAA ATG AAG AGC TTC ACC AAG GCT TTT ATT TCA AGA GCT AAT         5368
Phe Asp Glu Met Lys Ser Phe Thr Lys Ala Phe Ile Ser Arg Ala Asn
                1710                1715                1720

ATA GGG CCC CGG CTC ACT CAA GTG TCG GTG CTG CAA TAT GGA AGC ATC         5416
Ile Gly Pro Arg Leu Thr Gln Val Ser Val Leu Gln Tyr Gly Ser Ile
                1725                1730                1735

ACC ACT ATC GAT GTG CCT TGG AAT GTA GCC TAT GAG AAA GTC CAT TTA         5464
Thr Thr Ile Asp Val Pro Trp Asn Val Ala Tyr Glu Lys Val His Leu
                1740                1745                1750

CTG AGC CTT GTG GAC CTC ATG CAG CAG GAG GGA GGC CCC AGC GAA ATT         5512
Leu Ser Leu Val Asp Leu Met Gln Gln Glu Gly Gly Pro Ser Glu Ile
1755                1760                1765                1770

GGG GAT GCT TTG AGC TTT GCC GTG CGA TAT GTC ACC TCA GAA GTC CAT         5560
Gly Asp Ala Leu Ser Phe Ala Val Arg Tyr Val Thr Ser Glu Val His
                1775                1780                1785

GGT GCC AGG CCC GGA GCC TCG AAA GCG GTG GTT ATC CTA GTC ACA GAT         5608
Gly Ala Arg Pro Gly Ala Ser Lys Ala Val Val Ile Leu Val Thr Asp
                1790                1795                1800

GTC TCC GTG GAT TCA GTG GAT GCT GCA GCC GAG GCC GCC AGA TCC AAC         5656
Val Ser Val Asp Ser Val Asp Ala Ala Ala Glu Ala Ala Arg Ser Asn
                1805                1810                1815

CGA GTG ACA GTG TTC CCC ATT GGA ATC GGG GAT CGG TAC AGT GAG GCC         5704
Arg Val Thr Val Phe Pro Ile Gly Ile Gly Asp Arg Tyr Ser Glu Ala
                1820                1825                1830

CAG CTG AGC AGC TTG GCA GGC CCA AAG GCT GGC TCC AAT ATG GTA AGG         5752
Gln Leu Ser Ser Leu Ala Gly Pro Lys Ala Gly Ser Asn Met Val Arg
1835                1840                1845                1850

CTC CAG CGA ATT GAA GAC CTC CCC ACC GTG GCC ACC CTG GGA AAT TCC         5800
Leu Gln Arg Ile Glu Asp Leu Pro Thr Val Ala Thr Leu Gly Asn Ser
                1855                1860                1865

TTC TTC CAC AAG CTG TGC TCT GGG TTT GAT AGA GTT TGC GTG GAT GAG         5848
Phe Phe His Lys Leu Cys Ser Gly Phe Asp Arg Val Cys Val Asp Glu
                1870                1875                1880

GAT GGG AAT GAG AAG AGG CCC GGG GAT GTC TGG ACC TTG CCA GAC CAG         5896
Asp Gly Asn Glu Lys Arg Pro Gly Asp Val Trp Thr Leu Pro Asp Gln
                1885                1890                1895

TGC CAC ACA GTG ACT TGC CTG CCA GAT GGC AGA ACC TTG CTG AAG AGT         5944
Cys His Thr Val Thr Cys Leu Pro Asp Gly Gln Thr Leu Leu Lys Ser
                1900                1905                1910

CAT CGG GTC AAC TGT GAC CGG GGG CCA AGG CCT TCG TGC CCC AAT GGC         5992
His Arg Val Asn Cys Asp Arg Gly Pro Arg Pro Ser Cys Pro Asn Gly
```

-continued

```
         1915                1920                1925                1930
CAG CCC CCT CTC AGG GTA GAG GAG ACC TGT GGC TGC CGC TGG ACC TGT         6040
Gln Pro Pro Leu Arg Val Glu Glu Thr Cys Gly Cys Arg Trp Thr Cys
            1935                1940                1945

CCC TGT GTG TGC ATG GGC AGC TCT ACC CGG CAC ATC GTG ACC TTT GAT         6088
Pro Cys Val Cys Met Gly Ser Ser Thr Arg His Ile Val Thr Phe Asp
            1950                1955                1960

GGG CAG AAT TTC AAG CTG ACT GGC AGC TGT TCG TAT GTC CTA TTT CAA         6136
Gly Gln Asn Phe Lys Leu Thr Gly Ser Cys Ser Tyr Val Leu Phe Gln
            1965                1970                1975

AAC AAG GAG CAG GAC CTG GAG GTG ATT CTC CAG AAT GGT GCC TGC AGC         6184
Asn Lys Glu Gln Asp Leu Glu Val Ile Leu Gln Asn Gly Ala Cys Ser
            1980                1985                1990

CCT GGG GCG AAG GAG ACC TGC ATG AAA TCC ATT GAG GTG AAG CAT GAC         6232
Pro Gly Ala Lys Glu Thr Cys Met Lys Ser Ile Glu Val Lys His Asp
1995                2000                2005                2010

GGC CTC TCA GTT GAG CTC CAC AGT GAC ATG CAG ATG ACA GTG AAT GGG         6280
Gly Leu Ser Val Glu Leu His Ser Asp Met Gln Met Thr Val Asn Gly
            2015                2020                2025

AGA CTA GTC TCC ATC CCA TAT GTG GGT GGA GAC ATG GAA GTC AAT GTT         6328
Arg Leu Val Ser Ile Pro Tyr Val Gly Gly Asp Met Glu Val Asn Val
            2030                2035                2040

TAT GGG ACC ATC ATG TAT GAG GTC AGA TTC AAC CAT CTT GGC CAC ATC         6376
Tyr Gly Thr Ile Met Tyr Glu Val Arg Phe Asn His Leu Gly His Ile
            2045                2050                2055

TTC ACA TTC ACC CCC CAA AAC AAT GAG TTC CAG CTG CAG CTC AGC CCC         6424
Phe Thr Phe Thr Pro Gln Asn Asn Glu Phe Gln Leu Gln Leu Ser Pro
            2060                2065                2070

AGG ACC TTT GCT TCG AAG ACA TAT GGT CTC TGT GGG ATC TGT GAT GAG         6472
Arg Thr Phe Ala Ser Lys Thr Tyr Gly Leu Cys Gly Ile Cys Asp Glu
2075                2080                2085                2090

AAC GGA GCC AAT GAC TTC ATT CTG AGG GAT GGG ACA GTC ACC ACA GAC         6520
Asn Gly Ala Asn Asp Phe Ile Leu Arg Asp Gly Thr Val Thr Thr Asp
            2095                2100                2105

TGG AAG GCA CTC ATC CAG GAA TGG ACC GTA CAG CAG CTT GGG AAG ACA         6568
Trp Lys Ala Leu Ile Gln Glu Trp Thr Val Gln Gln Leu Gly Lys Thr
            2110                2115                2120

TCC CAG CCT GTC CAT GAG GAG CAG TGT CCT GTC TCC GAA TTC TTC CAC         6616
Ser Gln Pro Val His Glu Glu Gln Cys Pro Val Ser Glu Phe Phe His
            2125                2130                2135

TGC CAG GTC CTC CTC TCA GAA TTG TTT GCC GAG TGC CAC AAG GTC CTC         6664
Cys Gln Val Leu Leu Ser Glu Leu Phe Ala Glu Cys His Lys Val Leu
            2140                2145                2150

GCT CCA GCC ACC TTT TAT GCC ATG TGC CAG CCC GAC AGT TGC CAC CCG         6712
Ala Pro Ala Thr Phe Tyr Ala Met Cys Gln Pro Asp Ser Cys His Pro
2155                2160                2165                2170

AAG AAA GTG TGT GAG GCG ATT GCC TTG TAT GCC CAC CTC TGT CGG ACC         6760
Lys Lys Val Cys Glu Ala Ile Ala Leu Tyr Ala His Leu Cys Arg Thr
            2175                2180                2185

AAA GGG GTC TGT GTG GAC TGG AGG AGG GCC AAT TTC TGT GCT ATG TCA         6808
Lys Gly Val Cys Val Asp Trp Arg Arg Ala Asn Phe Cys Ala Met Ser
            2190                2195                2200

TGT CCA CCA TCC CTG GTG TAC AAC CAC TGT GAG CAT GGC TGC CCT CGG         6856
Cys Pro Pro Ser Leu Val Tyr Asn His Cys Glu His Gly Cys Pro Arg
            2205                2210                2215

CTC TGT GAA GGC AAT ACA AGC TCC TGT GGG GAC CAA CCC TCG GAA GGC         6904
Leu Cys Glu Gly Asn Thr Ser Ser Cys Gly Asp Gln Pro Ser Glu Gly
            2220                2225                2230

TGC TTC TGC CCC CCA AAC CAA GTC ATG CTG GAA GGT AGC TGT GTC CCC         6952
```

```
Cys Phe Cys Pro Pro Asn Gln Val Met Leu Glu Gly Ser Cys Val Pro
2235                2240                2245                2250

GAG GAG GCC TGT ACC CAG TGC ATC AGC GAG GAT GGA GTC CGG CAC CAG        7000
Glu Glu Ala Cys Thr Gln Cys Ile Ser Glu Asp Gly Val Arg His Gln
                2255                2260                2265

TTC CTG GAA ACC TGG GTC CCA GCC CAC CAG CCT TGC CAG ATC TGC ACG        7048
Phe Leu Glu Thr Trp Val Pro Ala His Gln Pro Cys Gln Ile Cys Thr
                2270                2275                2280

TGC CTC AGT GGG CGG AAG GTC AAC TGT ACG TTG CAG CCC TGC CCC ACA        7096
Cys Leu Ser Gly Arg Lys Val Asn Cys Thr Leu Gln Pro Cys Pro Thr
                2285                2290                2295

GCC AAA GCT CCC ACC TGT GGC CCG TGT GAA GTG GCC CGC CTC CGC CAG        7144
Ala Lys Ala Pro Thr Cys Gly Pro Cys Glu Val Ala Arg Leu Arg Gln
                2300                2305                2310

AAC GCA GTG CAG TGC TGC CCG GAG TAC GAG TGT GTG TGT GAC CTG GTG        7192
Asn Ala Val Gln Cys Cys Pro Glu Tyr Glu Cys Val Cys Asp Leu Val
2315                2320                2325                2330

AGC TGT GAC CTG CCC CCG GTG CCT CCC TGC GAA GAT GGC CTC CAG ATG        7240
Ser Cys Asp Leu Pro Pro Val Pro Pro Cys Glu Asp Gly Leu Gln Met
                2335                2340                2345

ACC CTG ACC AAT CCT GGC GAG TGC AGA CCC AAC TTC ACC TGT GCC TGC        7288
Thr Leu Thr Asn Pro Gly Glu Cys Arg Pro Asn Phe Thr Cys Ala Cys
                2350                2355                2360

AGG AAG GAT GAA TGC AGA CGG GAG TCC CCG CCC TCT TGT CCC CCG CAC        7336
Arg Lys Asp Glu Cys Arg Arg Glu Ser Pro Pro Ser Cys Pro Pro His
                2365                2370                2375

CGG ACG CCG GCC CTT CGG AAG ACT CAG TGC TGT GAT GAG TAT GAG TGT        7384
Arg Thr Pro Ala Leu Arg Lys Thr Gln Cys Cys Asp Glu Tyr Glu Cys
                2380                2385                2390

GCA TGC AAC TGT GTC AAC TCC ACG GTG AGC TGC CCG CTT GGG TAC CTG        7432
Ala Cys Asn Cys Val Asn Ser Thr Val Ser Cys Pro Leu Gly Tyr Leu
2395                2400                2405                2410

GCC TCG GCT GTC ACC AAC GAC TGT GGC TGC ACC ACA ACA ACC TGC TTC        7480
Ala Ser Ala Val Thr Asn Asp Cys Gly Cys Thr Thr Thr Thr Cys Phe
                2415                2420                2425

CCT GAC AAG GTG TGT GTC CAC CGA GGC ACC ATC TAC CCT GTG GGC CAG        7528
Pro Asp Lys Val Cys Val His Arg Gly Thr Ile Tyr Pro Val Gly Gln
                2430                2435                2440

TTC TGG GAG GAG GCC TGT GAC GTG TGC ACC TGC ACG GAC TTG GAG GAC        7576
Phe Trp Glu Glu Ala Cys Asp Val Cys Thr Cys Thr Asp Leu Glu Asp
                2445                2450                2455

TCT GTG ATG GGC CTG CGT GTG GCC CAG TGC TCC CAG AAG CCC TGT GAG        7624
Ser Val Met Gly Leu Arg Val Ala Gln Cys Ser Gln Lys Pro Cys Glu
                2460                2465                2470

GAC AAC TGC CTG TCA GGC TTC ACT TAT GTC CTT CAT GAA GGC GAG TGC        7672
Asp Asn Cys Leu Ser Gly Phe Thr Tyr Val Leu His Glu Gly Glu Cys
2475                2480                2485                2490

TGT GGA AGG TGT CTG CCA TCT GCC TGT GAG GTG GTC ACT GGT TCA CCA        7720
Cys Gly Arg Cys Leu Pro Ser Ala Cys Glu Val Val Thr Gly Ser Pro
                2495                2500                2505

CGG GGC GAC GCC CAG TCT CAC TGG AAG AAT GTT GGC TCT CAC TGG GCC        7768
Arg Gly Asp Ala Gln Ser His Trp Lys Asn Val Gly Ser His Trp Ala
                2510                2515                2520

TCC CCT GAC AAC CCC TGC CTC ATC AAT GAG TGT GTC CGA GTG AAG GAA        7816
Ser Pro Asp Asn Pro Cys Leu Ile Asn Glu Cys Val Arg Val Lys Glu
                2525                2530                2535

GAG GTC TTT GTG CAA CAG AGG AAT GTC TCC TGC CCC CAG CTG AAT GTC        7864
Glu Val Phe Val Gln Gln Arg Asn Val Ser Cys Pro Gln Leu Asn Val
                2540                2545                2550
```

```
CCC ACC TGC CCC ACG GGC TTC CAG CTG AGC TGT AAG ACC TCA GAG TGT      7912
Pro Thr Cys Pro Thr Gly Phe Gln Leu Ser Cys Lys Thr Ser Glu Cys
2555                2560                2565                2570

TGT CCC ACC TGT CAC TGC GAG CCC CTG GAG GCC TGC TTG CTC AAT GGT      7960
Cys Pro Thr Cys His Cys Glu Pro Leu Glu Ala Cys Leu Leu Asn Gly
            2575                2580                2585

ACC ATC ATT GGG CCG GGG AAA AGT CTG ATG ATT GAT GTG TGT ACA ACC      8008
Thr Ile Ile Gly Pro Gly Lys Ser Leu Met Ile Asp Val Cys Thr Thr
                2590                2595                2600

TGC CGC TGC ACC GTG CCG GTG GGA GTC ATC TCT GGA TTC AAG CTG GAG      8056
Cys Arg Cys Thr Val Pro Val Gly Val Ile Ser Gly Phe Lys Leu Glu
            2605                2610                2615

GGC AGG AAG ACC ACC TGT GAG GCA TGC CCC CTG GGT TAT AAG GAA GAG      8104
Gly Arg Lys Thr Thr Cys Glu Ala Cys Pro Leu Gly Tyr Lys Glu Glu
2620                2625                2630

AAG AAC CAA GGT GAA TGC TGT GGG AGA TGT CTG CCT ATA GCT TGC ACC      8152
Lys Asn Gln Gly Glu Cys Cys Gly Arg Cys Leu Pro Ile Ala Cys Thr
2635                2640                2645                2650

ATT CAG CTA AGA GGA GGA CAG ATC ATG ACA CTG AAG CGT GAT GAG ACT      8200
Ile Gln Leu Arg Gly Gly Gln Ile Met Thr Leu Lys Arg Asp Glu Thr
                2655                2660                2665

ATC CAG GAT GGC TGT GAC AGT CAC TTC TGC AAG GTC AAT GAA AGA GGA      8248
Ile Gln Asp Gly Cys Asp Ser His Phe Cys Lys Val Asn Glu Arg Gly
            2670                2675                2680

GAG TAC ATC TGG GAG AAG AGA GTC ACG GGT TGC CCA CCT TTC GAT GAA      8296
Glu Tyr Ile Trp Glu Lys Arg Val Thr Gly Cys Pro Pro Phe Asp Glu
        2685                2690                2695

CAC AAG TGT CTG GCT GAG GGA GGA AAA ATC ATG AAA ATT CCA GGC ACC      8344
His Lys Cys Leu Ala Glu Gly Gly Lys Ile Met Lys Ile Pro Gly Thr
        2700                2705                2710

TGC TGT GAC ACA TGT GAG GAG CCA GAA TGC AAG GAT ATC ATT GCC AAG      8392
Cys Cys Asp Thr Cys Glu Glu Pro Glu Cys Lys Asp Ile Ile Ala Lys
2715                2720                2725                2730

CTG CAG CGT GTC AAA GTG GGA GAC TGT AAG TCT GAA GAG GAA GTG GAC      8440
Leu Gln Arg Val Lys Val Gly Asp Cys Lys Ser Glu Glu Glu Val Asp
                2735                2740                2745

ATT CAT TAC TGT GAG GGT AAA TGT GCC AGC AAA GCC GTG TAC TCC ATC      8488
Ile His Tyr Cys Glu Gly Lys Cys Ala Ser Lys Ala Val Tyr Ser Ile
            2750                2755                2760

CAC ATG GAG GAT GTG CAG GAC CAG TGC TCC TGC TGC TCG CCC ACC CAG      8536
His Met Glu Asp Val Gln Asp Gln Cys Ser Cys Cys Ser Pro Thr Gln
        2765                2770                2775

ACG GAG CCC ATG CAG GTG GCC CTG CGC TGC ACC AAT GGC TCC CTC ATC      8584
Thr Glu Pro Met Gln Val Ala Leu Arg Cys Thr Asn Gly Ser Leu Ile
        2780                2785                2790

TAC CAT GAG ATC CTC AAT GCC ATC GAA TGC AGG TGT TCC CCC AGG AAG      8632
Tyr His Glu Ile Leu Asn Ala Ile Glu Cys Arg Cys Ser Pro Arg Lys
2795                2800                2805                2810

TGC AGC AAG TGAGGCCACT GCCTGGATGC TACTGTCGCC TGCCTTACCC              8681
Cys Ser Lys
GACCTCACTG GACTGGCCAG AGTGCTGCTC AGTCCTCCTC AGTCCTCCTC CTGCTCTGCT    8741

CTTGTGCTTC CTGATCCCAC AATAAAGGTC AATCTTTCAC CTTGAAAAAA AAAAAAAAA     8801

A                                                                    8802

(2) INFORMATION FOR SEQ ID NO:2:

(i) SEQUENCE CHARACTERISTICS:
        (A) LENGTH: 2813 amino acids
        (B) TYPE: amino acid
        (D) TOPOLOGY: linear
```

(ii) MOLECULE TYPE: protein (xi) SEQUENCE DESCRIPTION: SEQ ID NO:2:

```
Met Ser Pro Thr Arg Leu Val Arg Val Leu Leu Ala Leu Ala Leu Ile
 1               5                  10                  15

Leu Pro Gly Lys Leu Cys Thr Lys Gly Thr Val Gly Arg Ser Ser Met
                20                  25                  30

Ala Arg Cys Ser Leu Leu Gly Gly Asp Phe Ile Asn Thr Phe Asp Glu
            35                  40                  45

Ser Met Tyr Ser Phe Ala Gly Asp Cys Ser Tyr Leu Leu Ala Gly Asp
    50                  55                  60

Cys Gln Glu His Ser Ile Ser Leu Ile Gly Gly Phe Gln Asn Asp Lys
65                  70                  75                  80

Arg Val Ser Leu Ser Val Tyr Leu Gly Glu Phe Phe Asp Ile His Leu
                85                  90                  95

Phe Val Asn Gly Thr Met Leu Gln Gly Thr Gln Ser Ile Ser Met Pro
                100                 105                 110

Tyr Ala Ser Asn Gly Leu Tyr Leu Glu Ala Glu Ala Gly Tyr Tyr Lys
            115                 120                 125

Leu Ser Ser Glu Ala Tyr Gly Phe Val Ala Arg Ile Asp Gly Asn Gly
130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Lys Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Arg Cys Lys Arg Val Ser Pro Pro Ser Ser
            195                 200                 205

Pro Cys Asn Val Ser Ser Asp Glu Val Gln Gln Val Leu Trp Glu Gln
210                 215                 220

Cys Gln Leu Leu Lys Ser Ala Ser Val Phe Ala Arg Cys His Pro Leu
225                 230                 235                 240

Val Asp Pro Glu Pro Phe Val Ala Leu Cys Glu Arg Thr Leu Cys Thr
                245                 250                 255

Cys Val Gln Gly Met Glu Cys Pro Cys Ala Val Leu Leu Glu Tyr Ala
            260                 265                 270

Arg Ala Cys Ala Gln Gln Gly Ile Val Leu Tyr Gly Trp Thr Asp His
            275                 280                 285

Ser Val Cys Arg Pro Ala Cys Pro Ala Gly Met Glu Tyr Lys Glu Cys
    290                 295                 300

Val Ser Pro Cys Thr Arg Thr Cys Gln Ser Leu His Val Lys Glu Val
305                 310                 315                 320

Cys Gln Glu Gln Cys Val Asp Gly Cys Ser Cys Pro Glu Gly Gln Leu
                325                 330                 335

Leu Asp Glu Gly His Cys Val Gly Ser Ala Glu Cys Ser Cys Val His
            340                 345                 350

Ala Gly Gln Arg Tyr Pro Pro Gly Ala Ser Leu Leu Gln Asp Cys His
            355                 360                 365

Thr Cys Ile Cys Arg Asn Ser Leu Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400
```

-continued

```
Asn Arg Tyr Phe Thr Phe Ser Gly Val Cys His Tyr Leu Leu Ala Gln
            405                 410                 415
Asp Cys Gln Asp His Thr Phe Ser Val Val Ile Glu Thr Val Gln Cys
            420                 425                 430
Ala Asp Asp Leu Asp Ala Val Cys Thr Arg Ser Val Thr Val Arg Leu
            435                 440                 445
Pro Gly His His Asn Ser Leu Val Lys Leu Lys Asn Gly Gly Gly Val
            450                 455                 460
Ser Met Asp Gly Gln Asp Ile Gln Ile Pro Leu Leu Gln Gly Asp Leu
465                 470                 475                 480
Arg Ile Gln His Thr Val Met Ala Ser Val Arg Leu Ser Tyr Gly Glu
            485                 490                 495
Asp Leu Gln Met Asp Ser Asp Val Arg Gly Arg Leu Leu Val Thr Leu
            500                 505                 510
Tyr Pro Ala Tyr Ala Gly Lys Thr Cys Gly Arg Gly Asn Tyr Asn
            515                 520                 525
Gly Asn Arg Gly Asp Asp Phe Val Thr Pro Ala Gly Leu Ala Glu Pro
            530                 535                 540
Leu Val Glu Asp Phe Gly Asn Ala Trp Lys Leu Leu Gly Ala Cys Glu
545                 550                 555                 560
Asn Leu Gln Lys Gln His Arg Asp Pro Cys Ser Leu Asn Pro Arg Gln
            565                 570                 575
Ala Arg Phe Ala Glu Glu Ala Cys Ala Leu Leu Thr Ser Ser Lys Phe
            580                 585                 590
Glu Pro Cys His Arg Ala Val Gly Pro Gln Pro Tyr Val Gln Asn Cys
            595                 600                 605
Leu Tyr Asp Val Cys Ser Cys Ser Asp Gly Arg Asp Cys Leu Cys Ser
            610                 615                 620
Ala Val Ala Asn Tyr Ala Ala Ala Val Ala Arg Arg Gly Val His Ile
625                 630                 635                 640
Ala Trp Arg Glu Pro Gly Phe Cys Ala Leu Ser Cys Pro Gln Gly Gln
            645                 650                 655
Val Tyr Leu Gln Cys Gly Thr Pro Cys Asn Met Thr Cys Leu Ser Leu
            660                 665                 670
Ser Tyr Pro Glu Glu Asp Cys Asn Glu Val Cys Leu Glu Ser Cys Phe
            675                 680                 685
Ser Pro Pro Gly Leu Tyr Leu Asp Glu Arg Gly Asp Cys Val Pro Lys
            690                 695                 700
Ala Gln Cys Pro Cys Tyr Tyr Asp Gly Glu Ile Phe Gln Pro Glu Asp
705                 710                 715                 720
Ile Phe Ser Asp His His Thr Met Cys Tyr Cys Glu Asp Gly Phe Met
            725                 730                 735
His Cys Thr Thr Ser Gly Gly Leu Gly Ser Leu Leu Pro Asn Pro Val
            740                 745                 750
Leu Ser Ser Pro Arg Cys His Arg Ser Lys Arg Ser Leu Ser Cys Arg
            755                 760                 765
Pro Pro Met Val Lys Leu Val Cys Pro Ala Asp Asn Pro Arg Ala Glu
            770                 775                 780
Gly Leu Glu Cys Ala Lys Thr Cys Gln Asn Tyr Asp Leu Gln Cys Met
785                 790                 795                 800
Ser Thr Gly Cys Val Ser Gly Cys Leu Cys Pro Gln Gly Met Val Arg
            805                 810                 815
```

-continued

His Glu Asn Arg Cys Val Ala Leu Glu Arg Cys Pro Cys Phe His Gln
            820                 825                 830

Gly Gln Glu Tyr Ala Pro Gly Glu Thr Val Lys Ile Asp Cys Asn Thr
            835                 840                 845

Cys Val Cys Arg Asp Arg Lys Trp Thr Cys Thr Asp His Val Cys Asp
    850                 855                 860

Ala Thr Cys Ser Ala Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Leu Arg Ile Leu Val Gly Asn Glu
                900                 905                 910

Gly Cys Ser Tyr Pro Ser Val Lys Cys Lys Lys Arg Val Thr Ile Leu
            915                 920                 925

Val Glu Gly Gly Glu Ile Glu Leu Phe Asp Gly Glu Val Asn Val Lys
    930                 935                 940

Lys Pro Met Lys Asp Glu Thr His Phe Glu Val Val Glu Ser Gly Gln
945                 950                 955                 960

Tyr Val Ile Leu Leu Leu Gly Lys Ala Leu Ser Val Val Trp Asp His
                965                 970                 975

Arg Leu Ser Ile Ser Val Thr Leu Lys Arg Thr Tyr Gln Glu Gln Val
            980                 985                 990

Cys Gly Leu Cys Gly Asn Phe Asp Gly Ile Gln Asn Asn Asp Phe Thr
    995                 1000                1005

Ser Ser Ser Leu Gln Ile Glu Glu Asp Pro Val Asp Phe Gly Asn Ser
    1010                1015                1020

Trp Lys Val Asn Pro Gln Cys Ala Asp Thr Lys Lys Val Pro Leu Asp
1025                1030                1035                1040

Ser Ser Pro Ala Val Cys His Asn Asn Ile Met Lys Gln Thr Met Val
                1045                1050                1055

Asp Ser Ser Cys Arg Ile Leu Thr Ser Asp Ile Phe Gln Asp Cys Asn
            1060                1065                1070

Arg Leu Val Asp Pro Glu Pro Phe Leu Asp Ile Cys Ile Tyr Asp Thr
    1075                1080                1085

Cys Ser Cys Glu Ser Ile Gly Asp Cys Thr Cys Phe Cys Asp Thr Ile
    1090                1095                1100

Ala Ala Tyr Ala His Val Cys Ala Gln His Gly Lys Val Val Ala Trp
1105                1110                1115                1120

Arg Thr Ala Thr Phe Cys Pro Gln Asn Cys Glu Glu Arg Asn Leu His
                1125                1130                1135

Glu Asn Gly Tyr Glu Cys Glu Trp Arg Tyr Asn Ser Cys Ala Pro Ala
            1140                1145                1150

Cys Pro Ile Thr Cys Gln His Pro Glu Pro Leu Ala Cys Pro Val Gln
            1155                1160                1165

Cys Val Glu Gly Cys His Ala His Cys Pro Pro Gly Lys Ile Leu Asp
    1170                1175                1180

Glu Leu Leu Gln Thr Cys Ile Asp Pro Glu Asp Cys Pro Val Cys Glu
1185                1190                1195                1200

Val Ala Gly Arg Arg Leu Ala Pro Gly Lys Lys Ile Ile Leu Asn Pro
            1205                1210                1215

Ser Asp Pro Glu His Cys Gln Ile Cys Asn Cys Asp Gly Val Asn Phe
            1220                1225                1230

Thr Cys Lys Ala Cys Arg Glu Pro Gly Ser Val Val Val Pro Pro Thr

-continued

```
                1235                1240                  1245

Asp Gly Pro Ile Gly Ser Thr Thr Ser Tyr Val Glu Asp Thr Ser Glu
    1250                1255                1260

Pro Pro Leu His Asp Phe His Cys Ser Arg Leu Leu Asp Leu Val Phe
1265                1270                1275                1280

Leu Leu Asp Gly Ser Ser Lys Leu Ser Glu Asp Glu Phe Glu Val Leu
                1285                1290                1295

Lys Val Phe Val Val Gly Met Met Glu His Leu His Ile Ser Gln Lys
            1300                1305                1310

Arg Ile Arg Val Ala Val Val Glu Tyr His Asp Gly Ser His Ala Tyr
            1315                1320                1325

Ile Glu Leu Lys Asp Arg Lys Arg Pro Ser Glu Leu Arg Arg Ile Thr
            1330                1335                1340

Ser Gln Val Lys Tyr Ala Gly Ser Glu Val Ala Ser Thr Ser Glu Val
1345                1350                1355                1360

Leu Lys Tyr Thr Leu Phe Gln Ile Phe Gly Lys Ile Asp Arg Pro Glu
                1365                1370                1375

Ala Ser Arg Ile Ala Leu Leu Leu Met Ala Ser Gln Glu Pro Ser Arg
            1380                1385                1390

Leu Ala Arg Asn Leu Val Arg Tyr Val Gln Gly Leu Lys Lys Lys Lys
            1395                1400                1405

Val Ile Val Ile Pro Val Gly Ile Gly Pro His Ala Ser Leu Lys Gln
    1410                1415                1420

Ile His Leu Ile Glu Lys Gln Ala Pro Glu Asn Lys Ala Phe Val Phe
1425                1430                1435                1440

Ser Gly Val Asp Glu Leu Glu Gln Arg Arg Asp Glu Ile Ile Asn Tyr
            1445                1450                1455

Leu Cys Asp Leu Ala Pro Glu Ala Pro Ala Pro Thr Gln His Pro Pro
            1460                1465                1470

Met Ala Gln Val Thr Val Gly Ser Glu Leu Leu Gly Val Ser Ser Pro
            1475                1480                1485

Gly Pro Lys Arg Asn Ser Met Val Leu Asp Val Val Phe Val Leu Glu
            1490                1495                1500

Gly Ser Asp Lys Ile Gly Glu Ala Asn Phe Asn Lys Ser Arg Glu Phe
1505                1510                1515                1520

Met Glu Glu Val Ile Gln Arg Met Asp Val Gly Gln Asp Arg Ile His
                1525                1530                1535

Val Thr Val Leu Gln Tyr Ser Tyr Met Val Thr Val Glu Tyr Thr Phe
            1540                1545                1550

Ser Glu Ala Gln Ser Lys Gly Glu Val Leu Gln Val Arg Asp Ile
            1555                1560                1565

Arg Tyr Arg Gly Gly Asn Arg Thr Asn Thr Gly Leu Ala Leu Gln Tyr
    1570                1575                1580

Leu Ser Glu His Ser Phe Ser Val Ser Gln Gly Asp Arg Glu Gln Val
1585                1590                1595                1600

Pro Asn Leu Val Tyr Met Val Thr Gly Asn Pro Ala Ser Asp Glu Ile
                1605                1610                1615

Lys Arg Met Pro Gly Asp Ile Gln Val Val Pro Ile Gly Val Gly Pro
            1620                1625                1630

His Ala Asn Val Gln Glu Leu Glu Lys Ile Gly Trp Pro Asn Ala Pro
            1635                1640                1645

Ile Leu Ile His Asp Phe Glu Met Leu Pro Arg Glu Ala Pro Asp Leu
    1650                1655                1660
```

-continued

```
Val Leu Gln Arg Cys Cys Ser Gly Glu Gly Leu Gln Ile Pro Thr Leu
1665                1670                1675                1680

Ser Pro Thr Pro Asp Cys Ser Gln Pro Leu Asp Val Val Leu Leu Leu
                1685                1690                1695

Asp Gly Ser Ser Ser Ile Pro Ala Ser Tyr Phe Asp Glu Met Lys Ser
                1700                1705                1710

Phe Thr Lys Ala Phe Ile Ser Arg Ala Asn Ile Gly Pro Arg Leu Thr
                1715                1720                1725

Gln Val Ser Val Leu Gln Tyr Gly Ser Ile Thr Thr Ile Asp Val Pro
                1730                1735                1740

Trp Asn Val Ala Tyr Glu Lys Val His Leu Leu Ser Leu Val Asp Leu
1745                1750                1755                1760

Met Gln Gln Glu Gly Gly Pro Ser Glu Ile Gly Asp Ala Leu Ser Phe
                1765                1770                1775

Ala Val Arg Tyr Val Thr Ser Glu Val His Gly Ala Arg Pro Gly Ala
                1780                1785                1790

Ser Lys Ala Val Val Ile Leu Val Thr Asp Val Ser Val Asp Ser Val
                1795                1800                1805

Asp Ala Ala Ala Glu Ala Ala Arg Ser Asn Arg Val Thr Val Phe Pro
                1810                1815                1820

Ile Gly Ile Gly Asp Arg Tyr Ser Glu Ala Gln Leu Ser Ser Leu Ala
1825                1830                1835                1840

Gly Pro Lys Ala Gly Ser Asn Met Val Arg Leu Gln Arg Ile Glu Asp
                1845                1850                1855

Leu Pro Thr Val Ala Thr Leu Gly Asn Ser Phe Phe His Lys Leu Cys
                1860                1865                1870

Ser Gly Phe Asp Arg Val Cys Val Asp Glu Asp Gly Asn Glu Lys Arg
                1875                1880                1885

Pro Gly Asp Val Trp Thr Leu Pro Asp Gln Cys His Thr Val Thr Cys
                1890                1895                1900

Leu Pro Asp Gly Gln Thr Leu Leu Lys Ser His Arg Val Asn Cys Asp
1905                1910                1915                1920

Arg Gly Pro Arg Pro Ser Cys Pro Asn Gly Gln Pro Pro Leu Arg Val
                1925                1930                1935

Glu Glu Thr Cys Gly Cys Arg Trp Thr Cys Pro Cys Val Cys Met Gly
                1940                1945                1950

Ser Ser Thr Arg His Ile Val Phe Asp Gly Gln Asn Phe Lys Leu
                1955                1960                1965

Thr Gly Ser Cys Ser Tyr Val Leu Phe Gln Asn Lys Glu Gln Asp Leu
                1970                1975                1980

Glu Val Ile Leu Gln Asn Gly Ala Cys Ser Pro Gly Ala Lys Glu Thr
1985                1990                1995                2000

Cys Met Lys Ser Ile Glu Val Lys His Asp Gly Leu Ser Val Glu Leu
                2005                2010                2015

His Ser Asp Met Gln Met Thr Val Asn Gly Arg Leu Val Ser Ile Pro
                2020                2025                2030

Tyr Val Gly Gly Asp Met Glu Val Asn Val Tyr Gly Thr Ile Met Tyr
                2035                2040                2045

Glu Val Arg Phe Asn His Leu Gly His Ile Phe Thr Phe Thr Pro Gln
                2050                2055                2060

Asn Asn Glu Phe Gln Leu Gln Leu Ser Pro Arg Thr Phe Ala Ser Lys
2065                2070                2075                2080
```

-continued

```
Thr Tyr Gly Leu Cys Gly Ile Cys Asp Glu Asn Gly Ala Asn Asp Phe
            2085                2090                2095
Ile Leu Arg Asp Gly Thr Val Thr Thr Asp Trp Lys Ala Leu Ile Gln
        2100                2105                2110
Glu Trp Thr Val Gln Gln Leu Gly Lys Thr Ser Gln Pro Val His Glu
        2115                2120                2125
Glu Gln Cys Pro Val Ser Glu Phe Phe His Cys Gln Val Leu Leu Ser
        2130                2135                2140
Glu Leu Phe Ala Glu Cys His Lys Val Leu Ala Pro Ala Thr Phe Tyr
2145                2150                2155                2160
Ala Met Cys Gln Pro Asp Ser Cys His Pro Lys Lys Val Cys Glu Ala
            2165                2170                2175
Ile Ala Leu Tyr Ala His Leu Cys Arg Thr Lys Gly Val Cys Val Asp
            2180                2185                2190
Trp Arg Arg Ala Asn Phe Cys Ala Met Ser Cys Pro Pro Ser Leu Val
            2195                2200                2205
Tyr Asn His Cys Glu His Gly Cys Pro Arg Leu Cys Glu Gly Asn Thr
            2210                2215                2220
Ser Ser Cys Gly Asp Gln Pro Ser Glu Gly Cys Phe Cys Pro Pro Asn
2225                2230                2235                2240
Gln Val Met Leu Glu Gly Ser Cys Val Pro Glu Glu Ala Cys Thr Gln
            2245                2250                2255
Cys Ile Ser Glu Asp Gly Val Arg His Gln Phe Leu Glu Thr Trp Val
            2260                2265                2270
Pro Ala His Gln Pro Cys Gln Ile Cys Thr Cys Leu Ser Gly Arg Lys
            2275                2280                2285
Val Asn Cys Thr Leu Gln Pro Cys Pro Thr Ala Lys Ala Pro Thr Cys
            2290                2295                2300
Gly Pro Cys Glu Val Ala Arg Leu Arg Gln Asn Ala Val Gln Cys Cys
2305                2310                2315                2320
Pro Glu Tyr Glu Cys Val Cys Asp Leu Val Ser Cys Asp Leu Pro Pro
            2325                2330                2335
Val Pro Pro Cys Glu Asp Gly Leu Gln Met Thr Leu Thr Asn Pro Gly
            2340                2345                2350
Glu Cys Arg Pro Asn Phe Thr Cys Ala Cys Arg Lys Asp Glu Cys Arg
            2355                2360                2365
Arg Glu Ser Pro Pro Ser Cys Pro Pro His Arg Thr Pro Ala Leu Arg
            2370                2375                2380
Lys Thr Gln Cys Cys Asp Glu Tyr Glu Cys Ala Cys Asn Cys Val Asn
2385                2390                2395                2400
Ser Thr Val Ser Cys Pro Leu Gly Tyr Leu Ala Ser Ala Val Thr Asn
            2405                2410                2415
Asp Cys Gly Cys Thr Thr Thr Thr Cys Phe Pro Asp Lys Val Cys Val
            2420                2425                2430
His Arg Gly Thr Ile Tyr Pro Val Gly Gln Phe Trp Glu Glu Ala Cys
            2435                2440                2445
Asp Val Cys Thr Cys Thr Asp Leu Glu Asp Ser Val Met Gly Leu Arg
            2450                2455                2460
Val Ala Gln Cys Ser Gln Lys Pro Cys Glu Asp Asn Cys Leu Ser Gly
2465                2470                2475                2480
Phe Thr Tyr Val Leu His Glu Gly Glu Cys Cys Gly Arg Cys Leu Pro
            2485                2490                2495
Ser Ala Cys Glu Val Val Thr Gly Ser Pro Arg Gly Asp Ala Gln Ser
```

-continued

```
                2500                2505                2510
His Trp Lys Asn Val Gly Ser His Trp Ala Ser Pro Asp Asn Pro Cys
            2515                2520                2525
Leu Ile Asn Glu Cys Val Arg Val Lys Glu Val Phe Val Gln Gln
            2530                2535                2540
Arg Asn Val Ser Cys Pro Gln Leu Asn Val Pro Thr Cys Pro Thr Gly
2545                2550                2555                2560
Phe Gln Leu Ser Cys Lys Thr Ser Glu Cys Cys Pro Thr Cys His Cys
                2565                2570                2575
Glu Pro Leu Glu Ala Cys Leu Leu Asn Gly Thr Ile Ile Gly Pro Gly
            2580                2585                2590
Lys Ser Leu Met Ile Asp Val Cys Thr Thr Cys Arg Cys Thr Val Pro
            2595                2600                2605
Val Gly Val Ile Ser Gly Phe Lys Leu Glu Gly Arg Lys Thr Thr Cys
            2610                2615                2620
Glu Ala Cys Pro Leu Gly Tyr Lys Glu Glu Lys Asn Gln Gly Glu Cys
2625                2630                2635                2640
Cys Gly Arg Cys Leu Pro Ile Ala Cys Thr Ile Gln Leu Arg Gly Gly
            2645                2650                2655
Gln Ile Met Thr Leu Lys Arg Asp Glu Thr Ile Gln Asp Gly Cys Asp
            2660                2665                2670
Ser His Phe Cys Lys Val Asn Glu Arg Gly Glu Tyr Ile Trp Glu Lys
            2675                2680                2685
Arg Val Thr Gly Cys Pro Pro Phe Asp Glu His Lys Cys Leu Ala Glu
            2690                2695                2700
Gly Gly Lys Ile Met Lys Ile Pro Gly Thr Cys Cys Asp Thr Cys Glu
2705                2710                2715                2720
Glu Pro Glu Cys Lys Asp Ile Ile Ala Lys Leu Gln Arg Val Lys Val
            2725                2730                2735
Gly Asp Cys Lys Ser Glu Glu Val Asp Ile His Tyr Cys Glu Gly
            2740                2745                2750
Lys Cys Ala Ser Lys Ala Val Tyr Ser Ile His Met Glu Asp Val Gln
            2755                2760                2765
Asp Gln Cys Ser Cys Cys Ser Pro Thr Gln Thr Glu Pro Met Gln Val
            2770                2775                2780
Ala Leu Arg Cys Thr Asn Gly Ser Leu Ile Tyr His Glu Ile Leu Asn
2785                2790                2795                2800
Ala Ile Glu Cys Arg Cys Ser Pro Arg Lys Cys Ser Lys
            2805                2810
```

(2) INFORMATION FOR SEQ ID NO:3:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

AGGGGGTTTC CAAAATGACA AAAGAGTGAG CCTCTCCGTG TATCTCGGAG AATTTTTCGA    60

-continued (2) INFORMATION FOR SEQ ID NO:4:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

CATTCATTTG TTTGTCAATG GTACCATGCT GCAGGGGACC CAAAGGTAAG TCAGAAGCCC    60

(2) INFORMATION FOR SEQ ID NO:5:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

GAATGTTCAG GTTAATATGG ACCCTGGGGA TCACTTTGCA ACCCCCTTGT TTTTTCAGAT    60

(2) INFORMATION FOR SEQ ID NO:6:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

GAGGGAGCCG GGGCCCAGAG ACAGGAAGTA AATGTGCCCA GGGAAAGTGA GTGGCAGGAC    60

(2) INFORMATION FOR SEQ ID NO:7:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

TGGGTGAAAG CCCCATATCC CGACTCCTGG TCAAGGAGAC TTTGCACCAA GGTCCCAGCC    60

(2) INFORMATION FOR SEQ ID NO:8:

(i) SEQUENCE CHARACTERISTICS:

(A) LENGTH: 60 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

CTGGAGCATG GGGTTGGGGT TGGAAGGTGG AGGGACATGG AGGAAATGCA TGAGAAGCAC        60

(2) INFORMATION FOR SEQ ID NO:9:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

GCTTCCTGAG CTCCTCCTTG TCCCACCAGC ATCTCCATGC CCTACGCCTC CAATGGGC         58

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

AAATGACAAA AGAGTGAGCC GGTC                                              24

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

AAGTCTCCTT GACCAGCGGT CGGG                                              24

DNA ENCODING VON WILLEBRAND FACTOR AND METHODS OF USE

This application claims benefit of Provisional application Ser. No. 60/020,998, filed Jul. 19, 1996.

FIELD OF THE INVENTION

This invention relates generally to canine von Willebrand factor (vWF), and more particularly, to the gene encoding vWF as well as a genetic defect that causes canine von Willebrand's disease.

BIOLOGICAL DEPOSITS

| SEQUENCE | ACCESSION NO. |
|---|---|
| Canine von Willebrand Factor | AF 099154 |

BACKGROUND OF THE INVENTION

In both dogs and humans, von willebrand's disease (vWD) is a bleeding disorder of variable severity that results from a quantitative or qualitative defect in von Willebrand factor (vWF) (Ginsburg, D. et al., Blood 79:2507–2519 (1992); Ruggeri, Z. M. et al., FASEB J 7:308–316 (1993); Dodds, W. J., Mod Vet Pract 681–686 (1984); Johnson, G. S. et al., JAVMA 176:1261–1263 (1988); Brooks, M., Probl In Vet Med 4:636–646 (1992)). This clotting factor has two known functions, stabilization of Factor VIII (hemophilic factor A) in the blood, and aiding the adhesion of platelets to the subendothelium, which allows them to provide hemostasis more effectively. If the factor is missing or defective, the patient, whether human or dog, may bleed severely.

The disease is the most common hereditary bleeding disorder in both species, and is genetically and clinically heterogenous. Three clinical types, called 1, 2, and 3 (formerly I, II, and III; see Sadler, J. E. et al., Blood 84:676–679 (1994) for nomenclature changes), have been described. Type 1 vWD is inherited in a dominant, incompletely penetrant fashion. Bleeding appears to be due to the reduced level of vWF rather than a qualitative difference. Although this is the most common form of vWD found in most mammals, and can cause serious bleeding problems, it is generally less severe than the other two types. In addition, a relatively inexpensive vasopressin analog (DDAVP) can help alleviate symptoms (Kraus, K. H. et al., Vet Surg 18:103–109 (1989)).

In Type 2 vWD, patients have essentially normal levels of vWF, but the factor is abnormal as determined by specialized tests (Ruggeri, Z. M., et al., FASEB J 7:308–316 (1993); Brooks, M., Probl In Vet Med 4:636–646 (1992)). This type is also inherited in a dominant fashion and has only rarely been described in dogs (Turrentine, M. A., et al., Vet Clin North Am Small Anim Pract 18:275 (1988)).

Type 3 vWD is the most severe form of the disease. It is inherited as an autosomal recessive trait, and affected individuals have no detectable vWF in their blood. Serious bleeding episodes require transfusions of blood or cryoprecipitate to supply the missing vWF. Heterozygous carriers have moderately reduced factor concentrations, but generally appear to have normal hemostasis.

Scottish terriers have Type 3 vWD (Dodds, W. J., Mod Vet Pract 681–686 (1984); Johnson, G. S. et al., JAVMA 176:1261–1263 (1988)). Homozygotes have no detectable vWF and have a severe bleeding disorder. Heterozygotes have reduced levels of the factor, and are clinically normal (Brooks, M. et al., JAVMA 200:1123–1127 (1992)). The prevalence of vWD among Scottish terriers including both heterozygotes and homozygotes has been variously estimated from 27–31% (Stokol, T. et al., Res. Vet Sci. 59:152–155 (1995); Brooks, M., Proc. 9th ACVIM Forum 89–91 (1991)).

Currently, detection of affected and carrier Scottish terrier dogs is done by vWF antigen testing (Benson, R. E. et al., Am J Vet Res 44:399–403 (1983); Stokol, T. et al., Res. Vet Sci. 59:152–155 (1995)) or by coagulation assays (Rosborough, T. K. et al., J. Lab. Clin. Med. 96:47–56 (1980); Read, M. S. et al., J. Lab. Clin. Med. 101:74–82 (1983)). These procedures yield variable results, as the protein-based tests can be influenced by such things as sample collection, sample handling, estrous, pregnancy, vaccination, age, and hypothyroidism (Strauss, H. S. et al., New Eng J Med 269:1251–1252 (1963); Bloom, A. L., Mayo Clin Proc 66:743–751 (1991); Stirling, Y. et al., Thromb Haemostasis 52:176–182 (1984); Mansell, P. D. et al., Br. Vet. J. 148:329–337 (1992); Avgeris, S. et al., JAVMA 196:921–924 (1990); Panciera, D. P. et al., JAVMA 205:1550–1553 (1994)). Thus, for example, a dog that tests within the normal range on one day, can test within the carrier range on another day. It is therefore difficult for breeders to use this information.

It would thus be desirable to provide the nucleic acid sequence encoding canine vWF. It would also be desirable to provide the genetic defect responsible for canine vWD. It would further be desirable to obtain the amino acid sequence of canine vWF. It would also be desirable to provide a method for detecting carriers of the defective vWF gene based on the nucleic acid sequence of the normal and defective vWF gene.

SUMMARY OF THE INVENTION

The present invention provides a novel purified and isolated nucleic acid sequence encoding canine vWF. A nucleic acid sequence containing the mutation that causes vWD in Scottish terriers, a single-base deletion in exon 4, is also provided. The nucleic acid sequences of the present invention may be used in methods for detecting carriers of the mutation that causes vWD. Such methods may be used by breeders to reduce the frequency of the disease-causing allele and the incidence of disease. In addition, the nucleic acid sequence of the canine vWF provided herein may be used to determine the genetic defect that causes vWD in other breeds as well as other species.

Additional objects, advantages, and features of the present invention will become apparent from the following description, taken in conjunction with the accompanying drawings.

BRIEF DESCRIPTION OF THE DRAWINGS

The various advantages of the present invention will become apparent to one skilled in the art by reading the following specification and by referencing the following drawings in which:

FIGS. 1A–1C is the nucleic acid sequence of the canine von Willebrand factor of the present invention;

FIGS. 2A–2C is a comparison of the human and canine prepro-von Willebrand factor amino acid sequences;

FIG. 4 illustrates the results of a method of the present invention used to detect the Scottish terrier vWD mutation; and FIG. 5 shows the Scottish terrier pedigree, which in turn illustrates segregation of the mutant and normal vWF alleles.

DETAILED DESCRIPTION OF THE PREFERRED EMBODIMENTS

Figure 3:
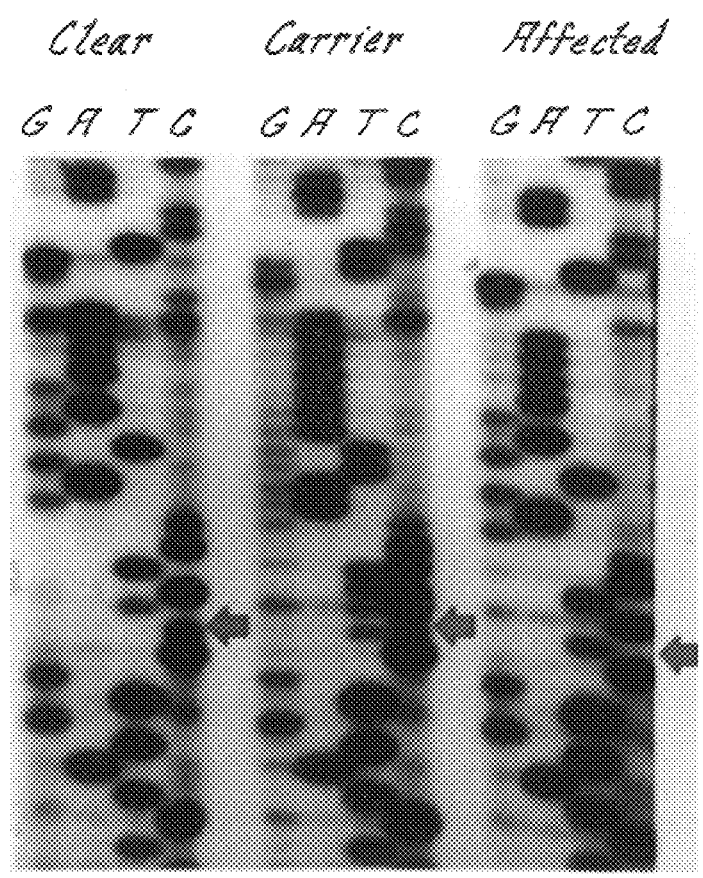
FIG. 3 provides nucleotide sequencing ladders for the von Willebrand's disease mutation region for normal (clear), carrier, and affected Scottish terriers, the sequences being obtained directly from PCR products derived from genomic DNAs in exon 4.
Figure 9:
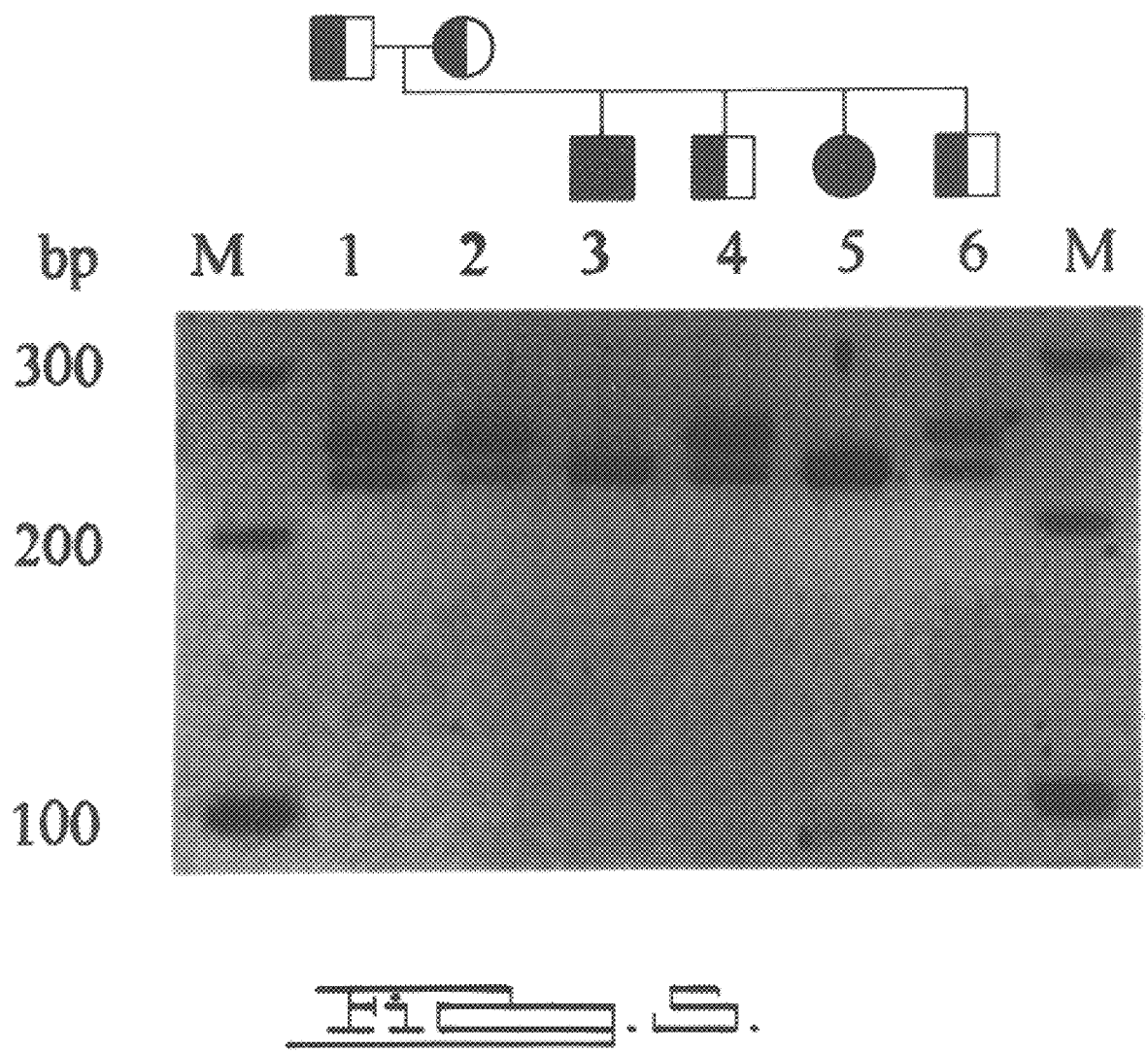

The cDNA encoding canine von Willebrand Factor (vWF) has been sequenced, and its sequence is set forth in FIGS. 1A–1C and SEQ ID NO: 1. The amino acid sequence corresponding to the cDNA of canine vWF has been subsequently deduced and is set forth in FIGS. 2A–2C and SEQ ID NO: 2. The mutation of the normal vWF gene which causes von Willebrand's Disease (vWD), a deletion at codon 88 of the normal gene resulting in a frameshift, is also provided. The nucleic acid sequences of the present invention may be used in methods for detecting homozygous and heterozygous carriers of the defective vWF gene.

In a preferred method of detecting the presence of the von Willebrand allele in canines, DNA samples are first collected by relatively noninvasive techniques, i.e., DNA samples are obtained with minimal penetration into body tissues of the animals to be tested. Common noninvasive tissue sample collection methods may be used and include withdrawing buccal cells via cheek swabs and withdrawing blood samples. Following isolation of the DNA by standard techniques, PCR is performed on the DNA utilizing pre-designed primers that produce enzyme restriction sites on those DNA samples that harbor the defective gene. Treatment of the amplified DNA with appropriate restriction enzymes such as BsiE I thus allows one to analyze for the presence of the defective allele. One skilled in the art will appreciate that this method may be applied not only to Scottish terriers, but to other breeds such as Shetland sheepdogs and Dutch Kooikers.

Overall, the present invention provides breeders with an accurate, definitive test whereby the undesired vWD gene may be eliminated from breeding lines. The current tests used by breeders are protein- based, and as noted previously, the primary difficulty with this type of test is the variability of results due to a variety of factors. The ultimate result of such variability is that an inordinate number of animals fall into an ambiguous grouping whereby carriers and noncarriers cannot be reliably distinguished. The present invention obviates the inherent limitations of protein-based tests by detecting the genetic mutation which causes vWD. As described in Specific Example 1, the methods of the present invention provide an accurate test for distinguishing noncarriers, homozygous carriers and heterozygous carriers of the defective vWF gene.

It will be appreciated that because the vWF cDNA of the present invention is substantially homologous to vWF cDNA throughout the canine species, the nucleic acid sequences of the present invention may be used to detect DNA mutations in other breeds as well. In addition, the canine vWF sequence presented herein potentially in combination with the established human sequence (Genbank Accession No. X04385, Bonthron, D. et al., *Nucleic Acids Res.* 14:7125–7128 (1986); Mancuso, D. J. et al., *Biochemistry* 30:253–269 (1989); Meyer, D. et al., *Throm Haemostasis* 70:99–104 (1993)), may be used to facilitate sequencing of the vWF gene and genetic defects causing vWD, in other mammalian species e.g., by using cross-species PCR methods known by those skilled in the art.

It is also within the contemplation of this invention that the isolated and purified nucleic acid sequences of the present invention be incorporated into an appropriate recombinant expression vector, e.g., viral or plasmid, which is capable of transforming an appropriate host cell, either eukaryotic (e.g., mammalian) or prokaryotic (e.g., *E. coli*). Such DNA may involve alternate nucleic acid forms, such as cDNA, gDNA, and DNA prepared by partial or total chemical synthesis. The DNA may also be accompanied by additional regulatory elements, such as promoters, operators and regulators, which are necessary and/or may enhance the expression of the vWF gene product. In this way, cells may be induced to over-express the. vWF gene, thereby generating desired amounts of the target vWF protein. It is further contemplated that the canine vWF polypeptide sequence of the present invention may be utilized to manufacture canine vWF using standard synthetic methods. One skilled in the art will also note that the defective protein encoded by the defective vWF gene of the present invention may also be of use in formulating a complementary diagnostic test for canine vWD that may provide further data in establishing the presence of the defective allele. Thus, production of the defective vWF polypeptide, either through expression in transformed host cells as described above for the active vWF polypeptide or through chemical synthesis, is also contemplated by the present invention.

The term "gene" as to referred herein means a nucleic acid which encodes a protein product. The term "nucleic acid" refers to a linear array of nucleotides and nucleosides, such as genomic DNA, cDNA and DNA prepared by partial or total chemical synthesis from nucleotides. The term "encoding" means that the nucleic acid may be transcribed and translated into the desired polypeptide. "Polypeptide" refers to amino acid sequences which comprise both full-length proteins and fragments thereof. "Mutation" as referred to herein includes any alteration in a nucleic acid sequence including, but not limited to, deletions, substitutions and additions.

As referred to herein, the term "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. In the present invention, hybridizing under either high or low stringency conditions would involve hybridizing a nucleic acid sequence (e.g., the complementary sequence to SEQ ID NO: 1 or portion thereof), with a second target nucleic acid sequence. "High stringency conditions" for the annealing process may involve, for example, high temperature and/or low salt content, which disfavor hydrogen bonding contacts among mismatched base pairs. "Low stringency conditions" would involve lower temperature, and/or lower salt concentration than that of high stringency conditions. Such conditions allow for two DNA strands to anneal if substantial, though not near complete complementarity exists between the two strands, as is the case among DNA strands that code for the same protein but differ in sequence due to the degeneracy of the genetic code. Appropriate stringency conditions which promote DNA hybridization, for example, 6X SSC at about 45° C., followed by a wash of 2X SSC at 50° C. are known to those skilled in the art or can be found in *Current Protocols in Molecular Biology,* John Wiley & Sons, NY (1989), 6.31–6.3.6. For example, the salt concentration in the wash step can be selected from a low stringency of about 2X SSC at 50° C. to a high stringency of about 0.2X SSC at 50° C. In addition, the temperature in the wash step can be increased from low stringency at room temperature, about 22° C., to high stringency conditions, at about 65° C. Other stringency parameters are described in Maniatis, T., et al., *Molecular Cloning: A Laboratory Manual,* Cold Spring Harbor Laboratory Press, Cold Spring N.Y., (1982), at pp. 387–389; see also Sambrook J. et al., *Molecular Cloning: A Laboratory Manual,* Second Edition, Volume 2, Cold Spring Harbor Laboratory Press, Cold Spring, N.Y. at pp. 8.46–8.47 (1989).

SPECIFIC EXAMPLE 1

Materials And Methods

Isolation of RNA. The source of the RNA was a uterus from a Scottish Terrier affected with vWD (factor level <0.1% and a clinical bleeder), that was surgically removed because of infection. Spleen tissue was obtained from a Doberman Pinscher affected with vWD that died from dilated cardiomyopathy (factor level 7% and a clinical bleeder). Total RNA was extracted from the tissues using Trizol (Life Technologies, Gaithersburg, Md.). The integrity of the RNA was assessed by agarose gel electrophoresis.

Design of PCR primer sets. Primers were designed to a few regions of the gene, where sequences from two species were available (Lavergne, J. M. et al., *Biochem Biophys Res Commun* 194:1019–1024 (1993); Bakhshi, M. R. et al., *Biochem Biophys Acta* 1132:325–328 (1992)). These primers were designed using rules for cross-species' amplifications (Venta et al., "Genes-Specific Universal Mammalian Sequence-Tagged Sites: Application To The Canine Genome" *Biochem. Genet.* (1996) in press). Most of the primers had to be designed to other regions of the gene using the human sequence alone (Mancuso, D. J. et al., *Biochemistry* 30:253–269 (1991)). Good amplification conditions were determined by using human and canine genomic DNAs.

Reverse Transcripase-PCR. Total RNA was reverse transcribed using random primers (Bergenhem, N. C. H. et al., *PNAS* (USA) 89:8789–8802 (1992)). The cDNA was amplified using the primer sets shown to work on canine genomic DNA.

DNA Sequence Analysis. Amplification products of the predicted sizes were isolated from agarose gels by adsorption onto silica gel particles using the manufacturer's method (Qiagen, Chatsworth, Calif.). Sequences were determined using $^{32}$P-5' end-labeled primers and a cycle sequencing kit (United States Biochemical Corp., Cleveland, Ohio). The sequences of the 5' and 3' untranslated regions were determined after amplification using Marathon™ RACE kits (Clontech, Palo Alto, Calif.). Sequences were aligned using the Eugene software analysis package (Lark Technologies, Houston, Tex.). The sequence of the canine intron four was determined from PCR-amplified genomic DNA.

Design of a Diagnostic Test. PCR mutagenesis was used to create diagnostic and control BsiE I and Sau96 I restriction enzyme sites for the test. Amplification conditions for the test are: 94° C., 1 min, 61° C., 1 min, and 72° C., 1 min, for 50 cycles using cheek swab DNA (Richards, B. et al., *Human Molecular Genetics* 2:159–163 (1992)).

Population Survey. DNA was collected from 87 Scottish terriers from 16 pedigrees. DNA was isolated either from blood using standard procedures (Sambrook, J. et al., Cold Harbor Spring Lab, Cold Harbor Spring N.Y., 2nd Edition, (1989)) or by cheek swab samples (Richards, B. et al., *Human Molecular Genetics* 2:159–163 (1992)). The genetic status of each animal in the survey was determined using the BsiE I test described above.

Results

Comparison of the canine and human sequences. The alignment of the canine and human prepro-von Willebrand Factor amino acid sequences is shown in FIGS. 2A–2C. The location of the Scottish terrier vWD mutation is indicated by the "★". Potential N-glycosylation sites are shown in bold type. The known and postulated integrin binding sites are boxed. Amino acid numbers are shown on the right side of the figure. The human sequence is derived from Genbank accession number X04385 (Bonthron, D. et al., *Nucleic Acids Res.* 14:7125–7128 (1986)).

Overall, 85.1% sequence identity is seen between the prepro-vWF sequences. The pro-region is slightly less conserved than the mature protein (81.4% vs. 87.5%). There were no other noteworthy percentage sequence identity differences seen in other regions of the gene, or between the known repeats contained within the gene (data not shown). Fourteen potential N-linked glycosylation sites are present in the canine sequence, all of which correspond to similar sites contained within the human sequence. The two integrin binding sites identified in the human vWF protein sequence (Lankhof, H. et al., *Blood* 86:1035–1042 (1995)) are conserved in the canine sequence as well (FIGS. 2A–2C). The 5' and 3' untranslated regions have diverged to a greater extent than the coding region (data not shown), comparable to that found between the human and bovine sequences derived for the 5' flanking region (Janel, N. et al., *Gene* 167:291–295 (1995)). Additional insights into the structure and function of the von Willebrand factor can be gained by comparison of the complete human sequence (Mancuso, D. J. et al., *Biochemistry* 30:253–269 (1989); Meyer, D. et al., *Throm Haemostasis* 70:99–104 (1993)) and the complete canine sequence reported here.

The sequence for most of exon 28 was determined (Mancuso, D. J. et al., *Thromb Haemost* 69:980 (1993); Porter, C. A. et al., *Mol Phylogenet Evol* 5:89–101 (1996)). All three sequences are in complete agreement, although two silent variants have been found in other breeds (Table 1, exon 28). Partial sequences of exons 40 and 41 (cDNA nucleotide numbers 6923 to 7155, from the initiation codon) were also determined as part of the development of a polymorphic simple tandem repeat genetic marker (Shibuya, H. et al., *Anim Genet* 24:122 (1994)). There is a single nucleotide sequence difference between this sequence ("T") and the sequence of the present invention, ("C") at nucleotide position 6928.

Scottish Terrier vWD mutation. FIG. 3 shows nucleotide sequencing ladders for the von Willebrand's Disease mutation region for normal (clear), carrier, and affected Scottish terriers. The sequences were obtained directly from PCR products derived from genomic DNAs in exon 4. The arrowheads show the location of the C nucleotide that is deleted in the disease-causing allele. Note that in the carrier ladder each base above the point of the mutation has a doublet appearance, as predicted for deletion mutations. The factor levels reported for these animals were: Normal, 54%; Carrier, 34%; Affected, <0.1%.

As a result of the deletion, a frameshift mutation at codon 88 leads to a new stop codon 103 bases downstream. The resulting severely truncated protein of 119 amino acids does not include any of the mature von Willebrand factor region. The identity of the base in the normal allele was determined from an unaffected dog.

Development of a diagnostic test. A PCR primer was designed to produce a BsiE I site in the mutant allele but not in the normal allele (FIG. 4). The position of the deleted nucleotide is indicated by an asterisk. The altered nucleotides in each primer are underlined. The normal and mutant allele can also be distinguished using Sau96 I. The naturally occurring Sau96 I sites are shown by double underlines. The highly conserved donor and acceptor dinucleotide splice sequences are shown in bold type.

In order to ensure that the restriction enzyme cut the amplified DNA to completion, an internal control restriction site common to both alleles was designed into the non-diagnostic primer. The test was verified by digestion of the DNA from animals that were affected, obligate carriers, or normal (based on high factor levels [greater than 100% of normal] obtained from commonly used testing labs and reported to us by the owners, and also using breeds in which Type 3 vWD has not been observed). The expected results were obtained (e.g., FIG. 5). Five vWD-affected animals from a colony founded from Scottish terriers (Brinkhous, K. M. et al., *Ann. New York Acad. Sci.* 370:191–203 (1981)) were also shown to be homozygous for this mutation. An additional unaffected animal from this same colony was found to be clear.

It would still be possible to misinterpret the results of the test if restriction enzyme digestion was not complete, and if the rates of cleavage of the cont778rol and diagnostic sites were vastly different. The rates of cleavage of the two BsiE I sites were thus examined by partially digesting the PCR products and running them on capillary electrophoresis. The rates were found to be very nearly equal (the diagnostic site is cut 12% faster than the control site).

The mutagenesis primer was also designed to produce a Sau96 I site into the normal allele but not the mutant allele. This is the reverse relationship compared to the BsiE I-dependent test, with respect to which allele is cut. Natural internal Sau96 I sites serve as digestion control sites (shown in FIG. 4). The test using this enzyme produced identical genotypic results compared to the BsiE I for all animals examined (data not shown).

A possible mutation in the Doberman Pinscher gene. The complete Scottish terrier sequence was compared to the complete Doberman Pinscher sequence. Several nucleotide differences were found and were compared to the nucleotides found in the same position in the human sequence as shown in Table 1 below. Most of these changes were silent. However, of three amino acid changes, one is relatively non-conservative (F905L) and is proposed to be the mutation that causes Doberman Pinscher vWD. Other data strongly suggest that the nucleotide interchange at the end of exon 43 causes a cryptic splice site to be activated reducing the amount of normally processed mRNA, with a concomitant decrease in the amount of vWF produced.

Mendelian inheritance. One test often used to verify the correct identification of a mutant allele is its inheritance according to Mendel's law of segregation. Three pedigrees were examined in which the normal and mutant alleles were segregating, as shown in FIG. 5. Exon four of the vWF gene was PCR-amplified from genomic DNA. The PCR products were examined for the presence of the normal and mutant vWF alleles by agarose gel electrophoresis after digestion with BsiE I (see FIG. 5). The affected animals are homozygous for the mutant allele (229 bp; lanes 3 and 5). The other animals in this pedigree are heterozygotes (251 bp and 229 bp; lanes 1, 2, 4, and 6), including the obligate carrier parents.

TABLE 1

Differences Between Scottie And Doberman Protein And Nucleotide von Willebrand Factor Sequences With Comparison To The Human Sequences

| Exon | A.A.[1] | Amino Acid | | | Codon | | |
|---|---|---|---|---|---|---|---|
| | | Human | Scottie | Doberman | Human | Scottie | Doberman |
| 5' UT[2] | nuc - 35[3] | N/A[4] | N/A | N/A | N/A | A | G |
| 4 | 85 | S | S/F Shift[5] | S | TCC | TCC/TC_ | TCC |
| 5 | 173 | M | R | K | ATG | AGG | AAG |
| 11 | 422 | S T | T | TCC | ACA | ACC | |
| 21 | 898 | C | C | C | TGC | TGT | TGC |
| 21 | 905 | F | F | L | TTT | TTC | TTA |
| 24 | 1041 | S | S | S | TCA | TCA | TCG |
| 24 | 1042 | S | S | S | TCC | TCC | TCA |
| 28 | 1333 | D | D | E | GAC | GAC | GAG |
| 28 | 1349 | Y | Y | Y | TAT | TAT | TAC* |

TABLE 1-continued

Differences Between Scottie And Doberman
Protein And Nucleotide von Willebrand Factor Sequences
With Comparison To The Human Sequences

| | | Amino Acid | | | Codon | | |
|---|---|---|---|---|---|---|---|
| Exon | A.A.[1] | Human | Scottie | Doberman | Human | Scottie | Doberman |
| 42 | 2381 | P | L | P | CCC | CTG | CCG |
| 43 | 2379 | S | S | S | TCG | TCG | TCA |
| 45 | 2555 | P | P | CCC | CCC | CCG | |
| 47 | 2591 | P/ P | P | CCC | CCT | CCC | |
| 49 | 2672 | D | D | D | GAT | GAT | GAC |
| 51 | 2744 | E | E | E | GAG | GAG | GAA |

[1]Amino acid residue position
[2]Untranslated region
[3]Nucleotide position
[4]Not Applicable
[5]Frameshift mutation
Boxed residues show amino acid differences between breeds
*This site has been shown to be polymorphic in some breeds
The mature VWF protein begins in exon 18

The alleles, as typed by both the BsiE I and Sau96 I tests, showed no inconsistencies with Mendelian inheritance. One of these pedigrees included two affected animals, two phenotypically normal siblings, and the obligate carrier parents. The two parents were found to be heterozygous by the test, the two affected animals were found to be homozygous for the mutant allele, and the normal siblings were found to be heterozygotes.

Population survey for the mutation. Cheek swabs or blood samples were collected from 87 animals in order to determine the incidence of carriers in the U.S. Scottish terrier population. Although we attempted to make the sample as random as possible, these dogs were found to come from 16 pedigrees, several of which are more distantly interconnected. This is due to some ascertainment bias, based on ownership (as opposed to phenotypic ascertainment bias). In these 87 animals four affected and 15 carrier animals were found.

Discussion

These results establish that the single base deletion found in exon four of the vWF gene causes vWD in the Scottish terrier breed. The protein produced from the mutant allele is extremely short and does not include any of the mature vWF protein. Four Scottish terriers known to be affected with the disease are homozygous for the mutation. Five other mixed-breed dogs descended from Scottish terriers, and affected with vWD, are also homozygous for the mutation. No normal animals are homozygous for the mutation. Unaffected obligate carriers are always heterozygous for the mutation.

The gene frequency, as determined from the population survey, appears to be around 0.13 resulting in a heterozygote frequency of about 23% and expected frequency of affected animals of about 2%. Although the sample size is relatively small and somewhat biased, these data are in general agreement with the protein-based surveys (Stokol, T. et al., *Res Vet Sci* 59:152–155 (1995); Brooks, M., *Probl In Vet Med* 4:636–646 (1992)), in that the allele frequency is substantial.

All data collected thus far indicate that this mutation accounts for essentially all of the von Willebrand's disease found in Scottish terriers. This result is consistent with the results found for other genetic diseases, defined at the molecular level, in various domestic animals (Shuster, D. E. et al., *PNAS* (USA) 89:9225–9229 (1992); Rudolph, J. A. et al., *Nat Genet* 2:144–147 (1992); O'Brien, P. J. et al., *JAVMA* 203:842–851 (1993)). A likely explanation may be found in the pronounced founder effect that occurs in domestic animals, compared to most human and wild animal populations.

Published data using the protein-based factor assays have shown that, at least in several instances, obligate carriers have had factor levels that would lead to a diagnosis of "clear" of the disease allele. For example, in one study an obligate carrier had a factor level of 78% (Johnson, G. S. et al., *JAVMA* 176:1261–1263 (1980)). In another study, at least some of the obligate carriers had factor levels of 65% or greater (Brinkhous, K. M. et al., *Ann. New York Acad. Sci.* 370:191–203 (1981)). In addition, the number of animals that fall into an equivocal range can be substantial. In one study, 19% of Scottish terriers fell in this range (50–65% of the normal vWF antigen level) (Stokol, T. et al., *Res Vet Sci* 59:152–155 (1995)). Thus, although the protein-based tests have been useful, the certainty of the DNA-based test described herein should relieve the necessity of repeated testing and the variability associated with the protein-based assays.

The mutation is present in the pre-vWF part of the molecule. This part of the molecule is processed off prior to delivery of the mature protein into the plasma. This pre-portion of the molecule is important for the assembly of the mature vWF protein (Verwiej, L. et al., *EBMO J* 6:2885–2890 (1987); Wise, R. J. et al., *Cell* 52:229–236 (1988)). With the Scottish terrier frameshift vWD mutation, neither this pre-portion nor any of the mature factor is ever produced, in keeping with the fact that no factor has ever been detected in the blood of affected dogs.

The determination of the complete canine vWF cDNA sequence will have an impact upon the development of carrier tests for other breeds and other species as well. Currently, Shetland sheepdogs and Dutch Kooikers are known to have a significant amount of Type 3 vWD (Brooks, M. et al., *JAVMA* 200:1123–1127 (1992); Slappendel, R. J., *Vet-Q* 17:S21–S22 (1995)). Type 3 vWD has occasionally be seen in other breeds as well (e.g., Johnson, G. S. et al., *JAVMA* 176:1261–1263 (1980)). All Type 3 vWD mutations described in humans to date have been found within the vWF gene itself. The availability of the canine sequence will make it easier to find the mutations in these breeds. In addition, at least some Type 1 mutations have been found within the human vWF gene, and thus Type 1 mutations may also be found within the vWF gene for breeds affected with that form of the disease. The availability of two divergent mammalian vWF cDNA sequences will also make it much easier to sequence the gene from other mammalian species using cross-species PCR methods (e.g., Venta et al., *Biochem. Genet.* (1996) in press).

The test described herein for the detection of the mutation in Scottish terriers may be performed on small amounts of DNA from any tissue. The tissues that are the least invasive to obtain are blood and buccal cells. For maximum convenience, a cheek swab as a source of DNA is preferred.

The foregoing discussion discloses and describes merely exemplary embodiments of the present invention. One skilled in the art will readily recognize from such discussion, and from the accompanying drawings, that various changes, modifications and variations can be made therein without departing from the spirit and scope of the invention.

All patents and other publications cited herein are expressly incorporated by reference.

We claim:

1. An isolated nucleic acid comprising a nucleotide sequence encoding the polypeptide of SEQ ID NO. 2.

2. The isolated nucleic acid of claim 1, wherein the nucleotide sequence is capable of hybridizing to SEQ ID NO. 1.

3. The isolated nucleic acid of claim 1, wherein the nucleotide sequence encodes the Scottish terrier von Willebrand Factor polypeptide.

4. The isolated nucleic acid of claim 2, wherein the nucleotide sequence encodes the Scottish terrier von Willebrand Factor polypeptide.

5. A vector comprising the nucleic acid of claim 1.

6. A vector comprising the nucleic acid of claim 2.

7. A cell comprising the vector of claim 5.

8. A cell comprising the vector of claim 6.

9. An isolated nucleic acid comprising a nucleotide sequence encoding the polypeptide of SEQ ID NO. 2 having a mutation.

10. The isolated nucleic acid of claim 9, wherein the nucleotide sequence is capable of hybridizing to the complement of SEQ ID NO. 1 having a base deletion at codon 88.

11. A vector comprising the nucleic acid of claim 9.

12. A vector comprising the nucleic acid of claim 10.

13. A cell comprising the vector of claim 11.

14. A cell comprising the vector of claim 12.

15. An isolated oligonucleotide sequence consisting of contiguous nucleotides of the nucleic acid sequence of SEQ ID NO. 1 and capable of specifically hybridizing with the canine von Willebrand Factor gene.

16. An isolated oligonucleotide sequence consisting of contiguous nucleotides of the nucleic acid sequence that is complementary to the sequence of SEQ ID NO. 1 and capable of specifically hybridizing with the canine von Willebrand Factor gene.

17. A method of detecting a canine von Willebrand Factor gene in a sample comprising the steps of:

a) contacting the sample with an oligonucleotide comprising contiguous nucleotides of the nucleic acid sequence of SEQ ID NO. 1 and capable of specifically hybridizing with the canine von Willebrand Factor gene, under conditions favorable for hybridization of the oligonucleotide to any complementary sequences of nucleic acid in the sample; and b) detecting hybridization, thereby detecting a canine von Willebrand Factor gene.

18. The method of claim 17, further comprising the step of:

c) quantifying hybridization of the oligonucleotide to complementary sequences.

19. The method of claim 17, wherein in SEQ ID NO. 1 there is a base deletion at codon 88.

20. An assay kit for screening for a canine von Willebrand Factor gene comprising:

a) an oligonucleotide comprising contiguous nucleotides of the nucleic acid sequence of SEQ ID NO. 1 and capable of hybridizing with the canine von Willebrand Factor gene;

b) reagents for hybridization of the oligonucleotide to a complementary nucleic acid sequence; and c) container means for a)–b).

21. A method of detecting a canine von Willebrand Factor gene in a sample comprising the steps of:

a) contacting the sample with an oligonucleotide comprising contiguous nucleotides of the nucleic acid sequence that is complementary to the sequence of SEQ ID NO. 1 and capable of specifically hybridizing to the complementary nucleotide sequence, under conditions favorable for hybridization of the oligonucleotide to any complementary sequences of nucleic acid in the sample; and b) detecting hybridization, thereby detecting a canine von Willebrand Factor gene.

22. The method of claim 21, further comprising the step of:

c) quantifying hybridization of the oligonucleotide to complementary sequences.

23. The method of claim 21, wherein in SEQ ID NO. 1 there is a base deletion at codon 88.

24. An assay kit for screening for a canine von Willebrand Factor gene comprising:

a) an oligonucleotide comprising contiguous nucleotides from the nucleic acid sequence that is complementary to the sequence of SEQ ID NO. 1 and capable of specifically hybridizing to the complementary nucleotide sequence;

b) reagents for hybridization of the oligonucleotide to a complementary nucleic acid sequence; and c) container means for a)–b).

25. The assay kit of claim 24, wherein in SEQ ID NO. 1 there is a base deletion at codon 88.

26. A method for detecting a mutation in the nucleotide sequence encoding the polypeptide of SEQ ID NO: 2 in a canine DNA sample comprising the steps of:

a) amplifying the DNA sample by polymerase chain reaction to produce polymerase chain reaction products, wherein the polymerase chain reaction uses primers that produce a restriction site in a mutant allele but not in a normal allele;

b) digesting the polymerase chain reaction products with a restriction enzyme specific to the restriction site of the restriction site primer to produce DNA fragments; and c) detecting the DNA fragments, thereby detecting a mutation in the nucleotide sequence encoding the polypeptide of SEQ ID NO: 2.

27. The method of claim 26, wherein the primers are those of SEQ ID NOS: 10 and 11.

28. The method of claim 26, wherein the DNA fragments are detected by gel electrophoresis.

29. The method of claim 27, wherein the restriction enzyme is BsiEI.

30. The method of claim 27, wherein the restriction enzyme is Sau96 I.

31. An oligonucleotide probe capable of detecting a mutation associated with canine von Willebrand's disease, wherein the mutation is a base deletion at codon 88 of SEQ ID NO. 1.

* * * * *

UNITED STATES PATENT AND TRADEMARK OFFICE
CERTIFICATE OF CORRECTION

PATENT NO.   : 6,040,143
DATED        : March 21, 2000
INVENTOR(S)  : Patrick J. Venta et al.

It is certified that error appears in the above-identified patent and that said Letters Patent is hereby corrected as shown below:

<u>Title page,</u>
Item [73], Assignees: The Regents of the University of Michigan, Ann Arbor, Michigan and Board of Trustees operating Michigan State University, East Lansing, Michigan

Signed and Sealed this

Thirteenth Day of August, 2002

Attest:

Attesting Officer

JAMES E. ROGAN
*Director of the United States Patent and Trademark Office*